(12) United States Patent
Nanayakkara

(10) Patent No.: US 12,710,198 B2
(45) **Date of Patent: *Aug. 18, 2026**

(54) AIRBORN PATHOGEN DISENFECTING SYSTEM WITH INTERCHANGEABLE FILTERS FOR AN HVAC SYSTEM

(71) Applicant: Pravin Nanayakkara, Boca Raton, FL (US)

(72) Inventor: Pravin Nanayakkara, Boca Raton, FL (US)

( * ) Notice: Subject to any disclaimer, the term of this patent is extended or adjusted under 35 U.S.C. 154(b) by 535 days.

This patent is subject to a terminal disclaimer.

(21) Appl. No.: 18/092,238

(22) Filed: Dec. 31, 2022

(65) Prior Publication Data

US 2023/0135061 A1 May 4, 2023

Related U.S. Application Data

(63) Continuation-in-part of application No. 17/244,670, filed on Apr. 29, 2021, now Pat. No. 11,660,367.

(51) Int. Cl.

| | |
|---|---|
| ***F24F 13/28*** | (2006.01) |
| ***A61L 2/22*** | (2006.01) |
| ***A61L 9/20*** | (2006.01) |
| ***F24F 8/108*** | (2021.01) |
| ***F24F 8/125*** | (2021.01) |
| ***F24F 8/22*** | (2021.01) |
| ***F24F 8/24*** | (2021.01) |

(52) U.S. Cl.
CPC ................ *F24F 13/28* (2013.01); *A61L 2/22* (2013.01); *A61L 9/20* (2013.01); *F24F 8/108* (2021.01); *F24F 8/125* (2021.01); *F24F 8/22* (2021.01); *F24F 8/24* (2021.01); *A61L 2202/15* (2013.01); *A61L 2209/12* (2013.01); *A61L 2209/14* (2013.01); *A61L 2209/15* (2013.01); *A61L 2209/16* (2013.01)

(58) Field of Classification Search
None
See application file for complete search history.

(56) References Cited

U.S. PATENT DOCUMENTS 6,264,713 B1 * 7/2001 Lewis, II ............ B01D 46/521 55/502
2013/0034470 A1 * 2/2013 Wang .................... B01D 53/88 29/428

* cited by examiner

*Primary Examiner* — Jelitza M Perez
(74) *Attorney, Agent, or Firm* — Melvin K. Silverman

(57) ABSTRACT

The present invention provides for a system for disinfecting air circulated in an HVAC system. The system includes an interchangeable filter located in a filter housing. The filter housing connects two segments of ductwork. The filter housing is contoured to align with perimeter dimensions of each of said two segments of ductwork. The filter housing defining a four-walled metallic segment with openings correlating to each of said two segments of ductwork. A closeable opening provides for insertion of the interchangeable filter therein created by a hinge moveably coupling one wall of said four-walled metallic segment thereby creating a hinged flap, whereby once closed, the flap seals an inside airflow channel between each ductwork segment connected by said four-walled metallic segment.

1 Claim, 40 Drawing Sheets

12
14
16
18
34
22
24
22
32
30

28
20
16
22
24
28
32

62a
64a
68a 62a
64a
66a
72a 68a
66a
72a 62a
68a
66a
79a
64a
72a 68a
62a
64a
66a
72a

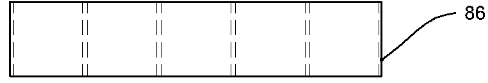
Fig. 22A
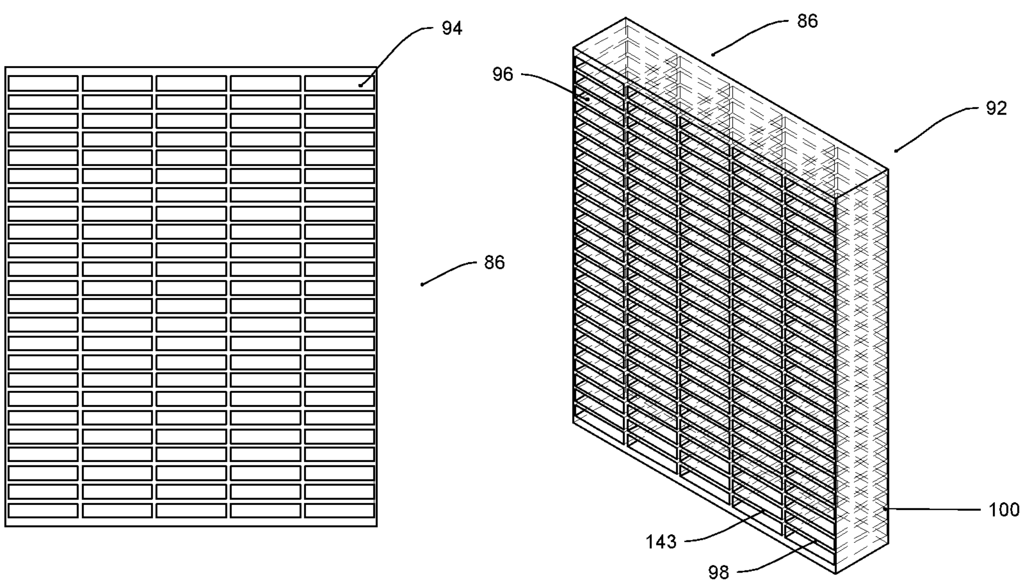
Fig. 22B
Fig. 22C

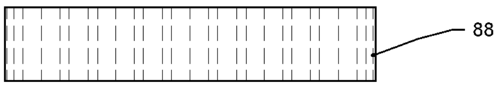
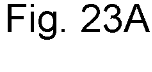
Fig. 23A
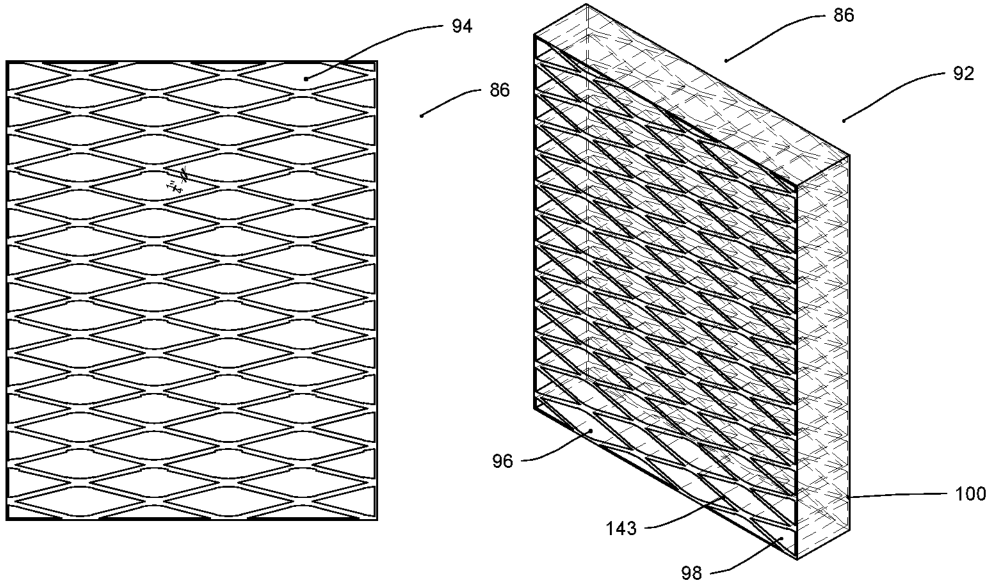
Fig. 23B
Fig. 23C

Fig. 24A
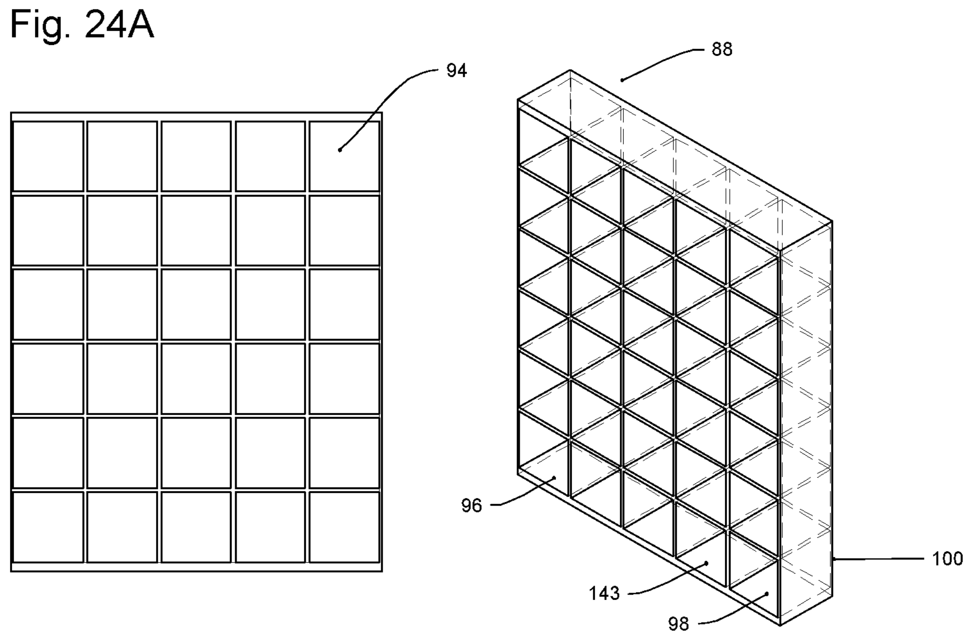
Fig. 24B
Fig. 24C 38
14
54
62b
102
14
AIR FLOW
AIR FLOW
40

38
14
54
62b
102
14
AIR FLOW
AIR FLOW
40
102
AIR FLOW
INTAKE 62b
64b
68b 66b
64a
72b 68b
62b
66b
62b
104
106
72b 66b
106
104
74b
64b
68b
66b
72b 68b
64b
66b
104
106
70b
72b 60b
78b 80b
60b
SECT.
29D 78b
60a 82b
78b
84b 78b
82b
78b
60b
84b

AIRBORN PATHOGEN DISENFECTING SYSTEM WITH INTERCHANGEABLE FILTERS FOR AN HVAC SYSTEM

CROSS REFERENCE TO RELATED APPLICATIONS

The application is a continuation-in-part of application Ser. No. 17/244,670, filed Apr. 29, 2021. All prior related patents and patent applications are herein incorporated by reference in their entirety.

FIELD OF THE INVENTION

The present invention relates to an enhanced HVAC system with interchangeable filters.

BACKGROUND OF THE INVENTION

The typical air duct system incorporates a chiller tower and one condenser along with ductwork and a filter. These existing systems were designed to carry hot or cold air to a room. There is no antimicrobial filter or system to kill viruses and bacteria that can slip through the existing filters. People purchase aerosols and spray as needed. Spraying may take care of an immediate problem, however it does not provide prolonged sanitation and is not thorough enough to constantly provide a sanitary product. The aerosol may last for the moment in which it was sprayed but 5 to 10 minutes later it is no longer present in the air.

While vaccines work to help keep people's immunities strong against viruses and other pathogens, each year new viruses enter and spread through the population. When such a spread turns into an event of concern, the implementation of systems to help curb the spread are necessary. While much advancement has been made in filter technology, HVAC systems as a whole are largely unchanged.

Thus, a need in the industry has arisen for air-disinfecting system for HVAC systems is necessary to meet the current demand for increased air quality free or substantially free from airborne pathogens.

SUMMARY OF THE INVENTION

The present invention provides for a system for disinfecting air circulated in an HVAC system. The system includes an interchangeable filter located in a filter housing. The filter housing connects two segments of ductwork. The filter housing is contoured to align with perimeter dimensions of each of said two segments of ductwork. The filter housing defining a four-walled metallic segment with openings correlating to each of said two segments of ductwork. A closeable opening provides for insertion of the interchangeable filter therein created by a hinge moveably coupling one wall of said four-walled metallic segment thereby creating a hinged flap, whereby once closed, the flap seals an inside airflow channel between each ductwork segment connected by said four-walled metallic segment.

It is an object of this invention to provide a system capable of killing airborne pathogens.

It is yet further an object of this invention to provide a system that can be easily installed or retrofitted into an existing system.

It is an additional object of this invention to provide modular and replaceable components to the system to allow maximum efficiency in disinfecting the air circulating in and out of the HVAC system.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 19B is an embodiment of a filter used with the replaceable filter system shown in FIG. 18D.

FIG. 19C is an embodiment of a filter used with the replaceable filter system shown in FIG. 18D.

FIG. 22A is a top view of the filter shown in FIG. 19A.

FIG. 22B is a front view of the filter shown in FIG. 19A.

FIG. 22C is a perspective view of the filter shown in FIG. 19A.

FIG. 23A is a top view of the filter shown in FIG. 19B.

FIG. 23B is a front view of the filter shown in FIG. 19B.

FIG. 23C is a perspective view of the filter shown in FIG. 19B.

FIG. 24A is a top view of the filter shown in FIG. 19C.

FIG. 24B is a front view of the filter shown in FIG. 19C.

FIG. 24C is a perspective view of the filter shown in FIG. 19C.

DETAILED DESCRIPTION OF THE INVENTION

As described in the background of the invention, the typical air duct system incorporates a chiller tower and one condenser along with ductwork and a filter. These existing systems were designed to carry hot or cold air to a room. There is no antimicrobial filter or system to kill viruses and bacteria that can slip through the existing filters. People purchase aerosols and spray as needed. Spraying may take care of an immediate problem, however it does not provide prolonged sanitation and is not thorough enough to constantly provide a sanitary product. The aerosol may last for the moment in which it was sprayed but 5 to 10 minutes later it is no longer present in the air.

The present invention provides a multi-stage and multi-component disinfecting system for an HVAC system 10, which solves the long felt need for a thorough and reliable system of disinfecting the air in an HVAC system.

Figure 1:
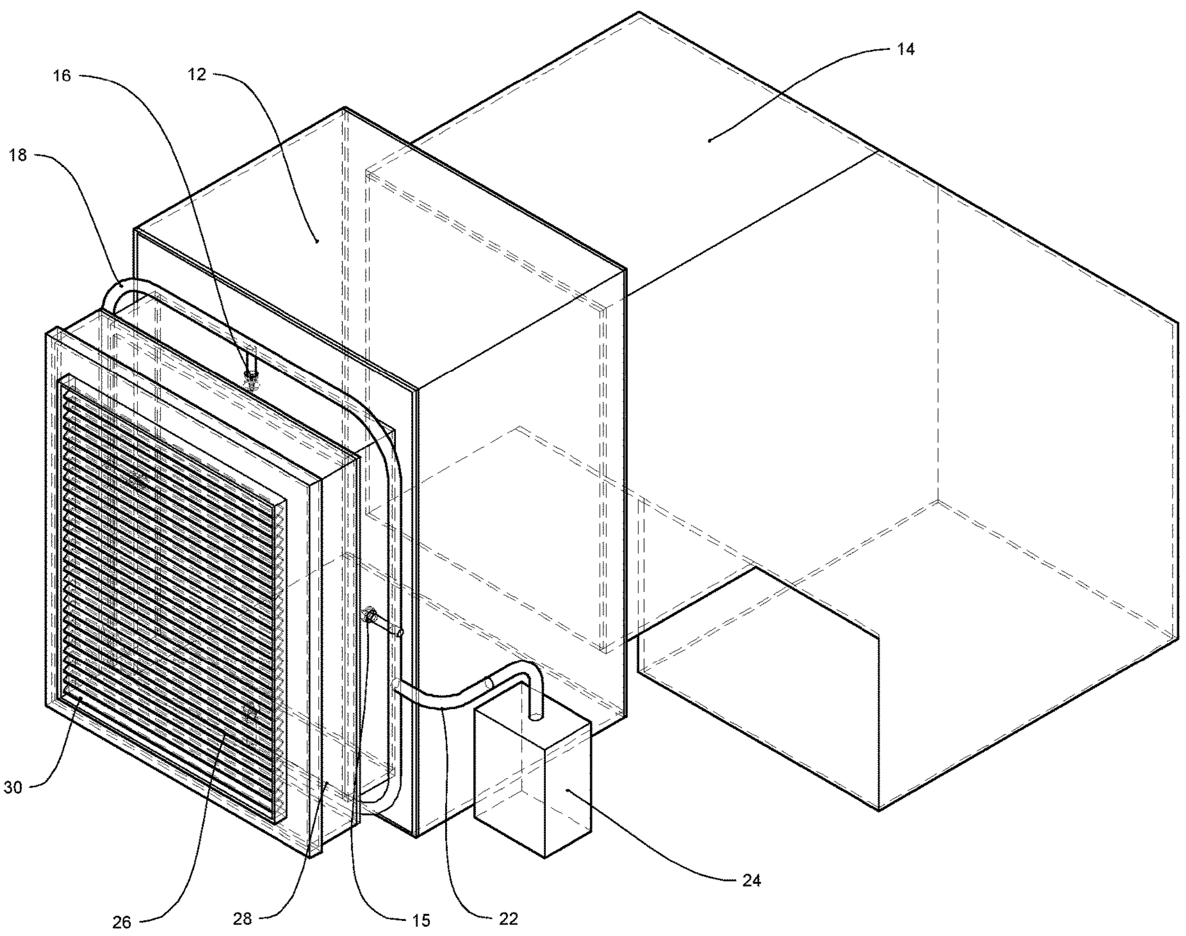
FIG. 1 is a perspective view of an air intake of the system.
Figures 2A, 2B:
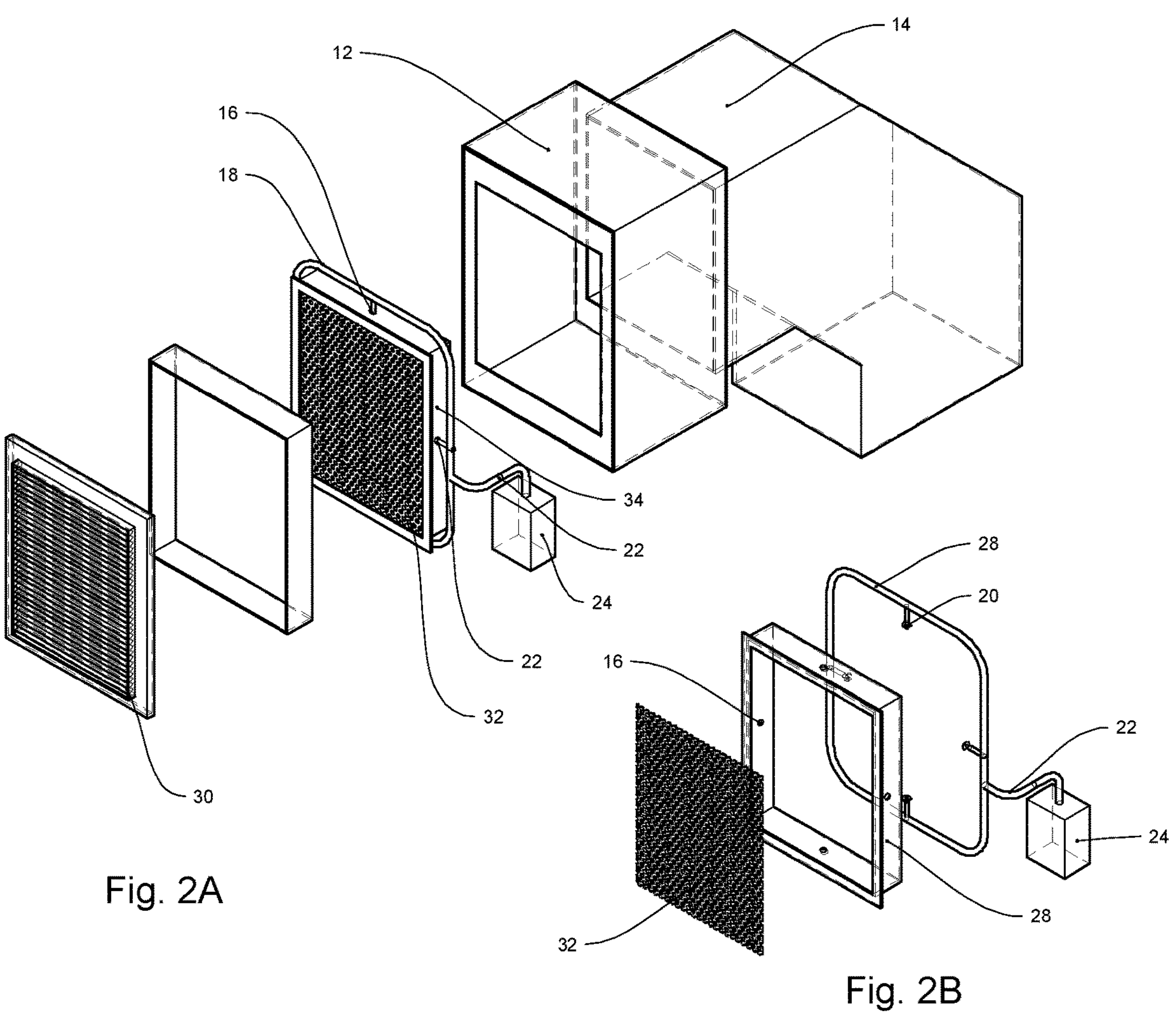
FIG. 2A is an exploded view of perspective view of FIG. 1.
FIG. 2B is an exploded view of the disinfecting element of FIG. 2A.
Figure 3:
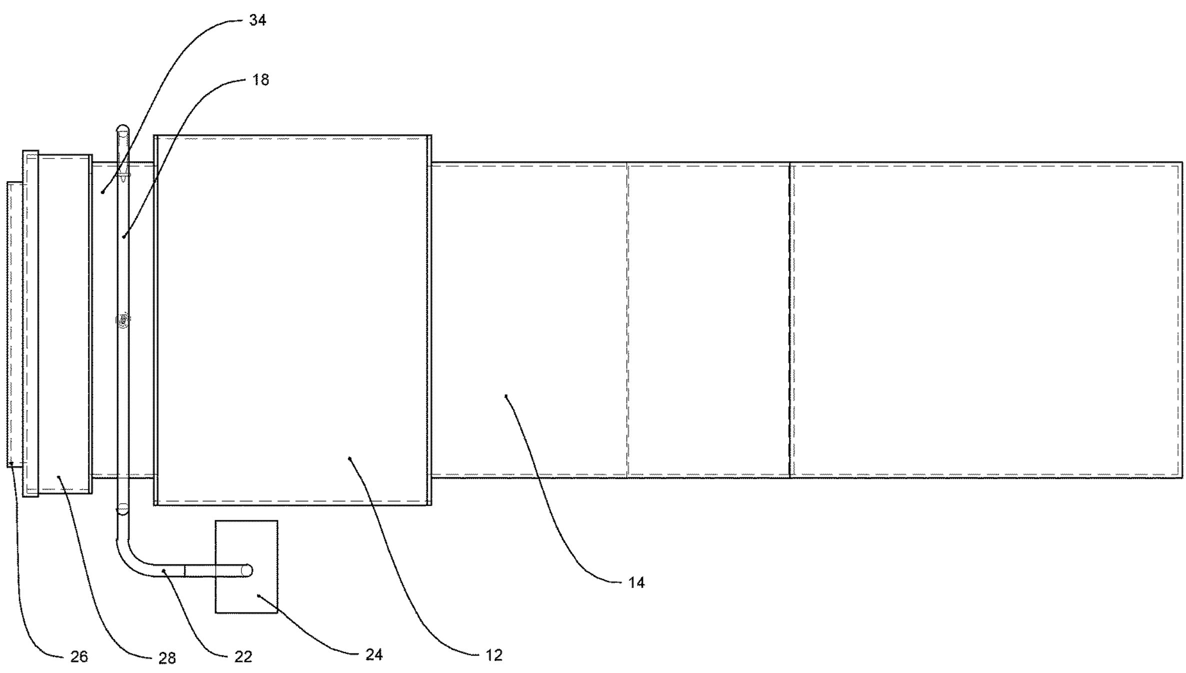
FIG. 3 Is a top view of the air intake of the system.
Figure 4:
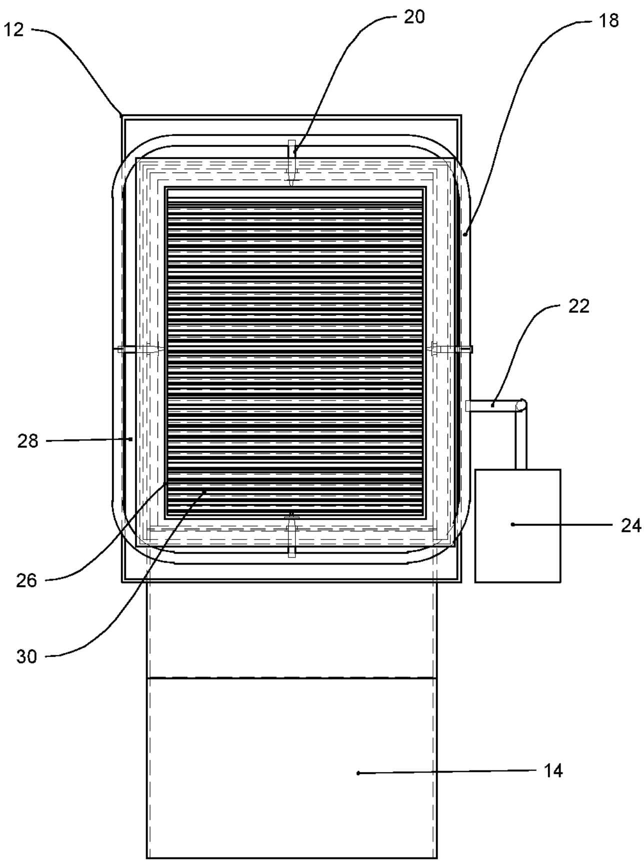
FIG. 4 is a front view of the air intake of the system.
Figure 5A:
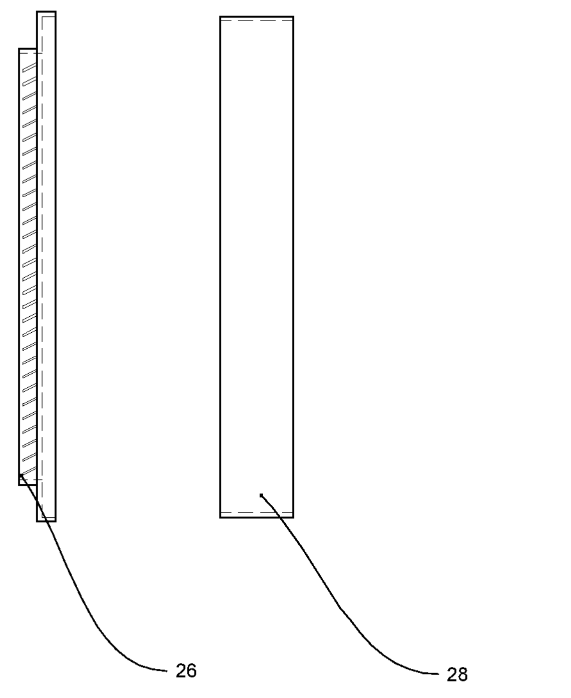
FIG. 5A is an exploded view of the disinfecting element of FIG. 5B.
Figure 5A:
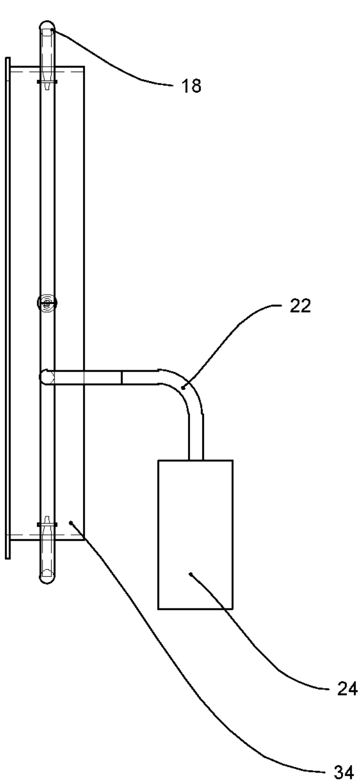
Figure 5B:
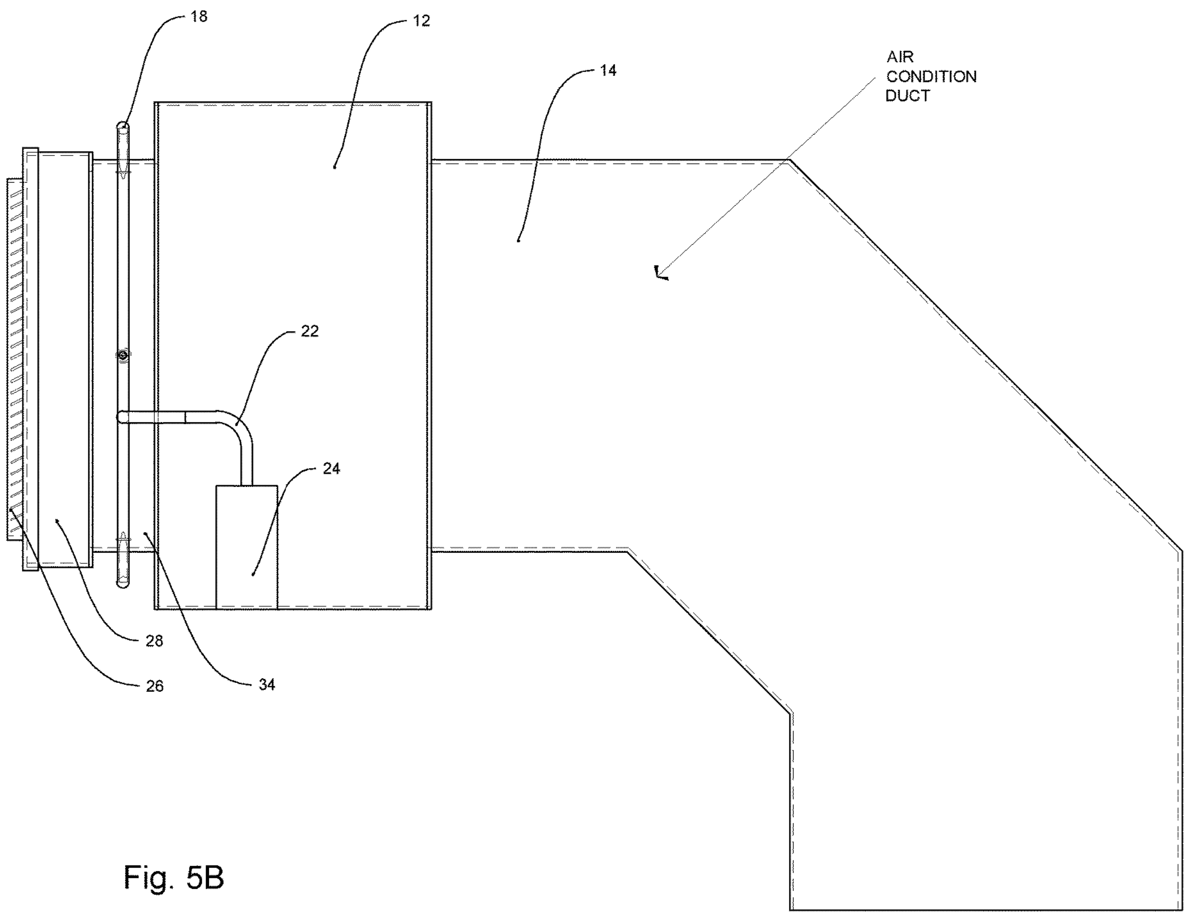
FIG. 5B is a side view of the air intake of the system.
Figure 6:
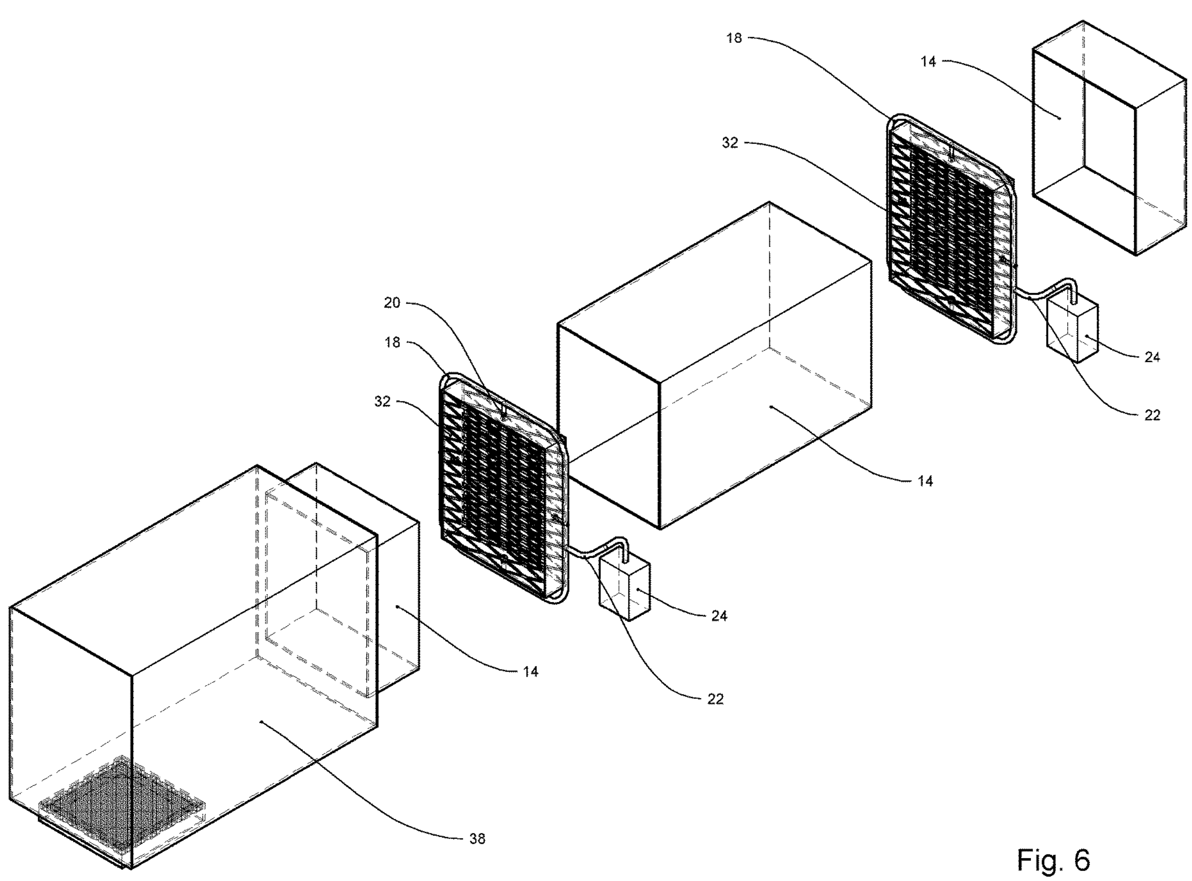
FIG. 6 is an exploded perspective view of the air handler of the system with cent shown in phantom.
Figure 7:
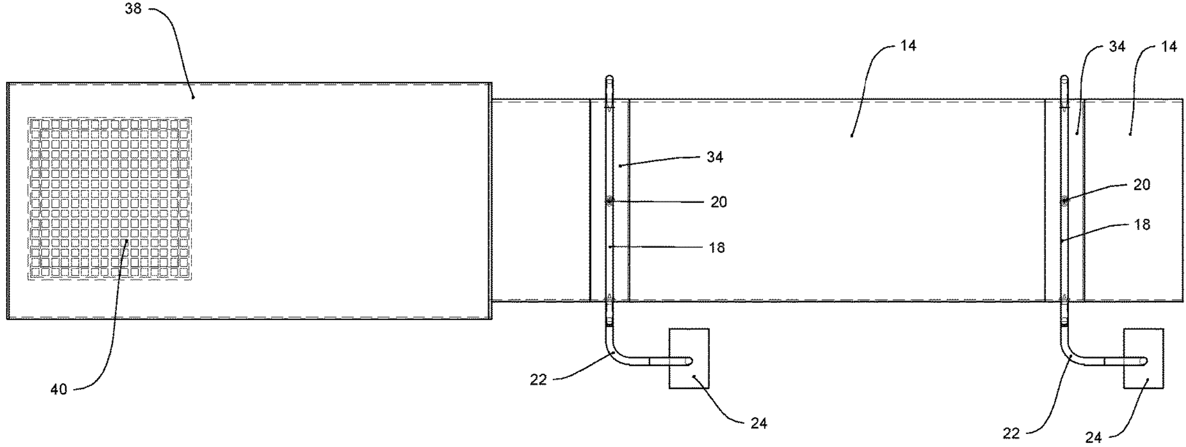
FIG. 7 is a top view of the air handler of the system with vent shown in phantom.
Figure 8:
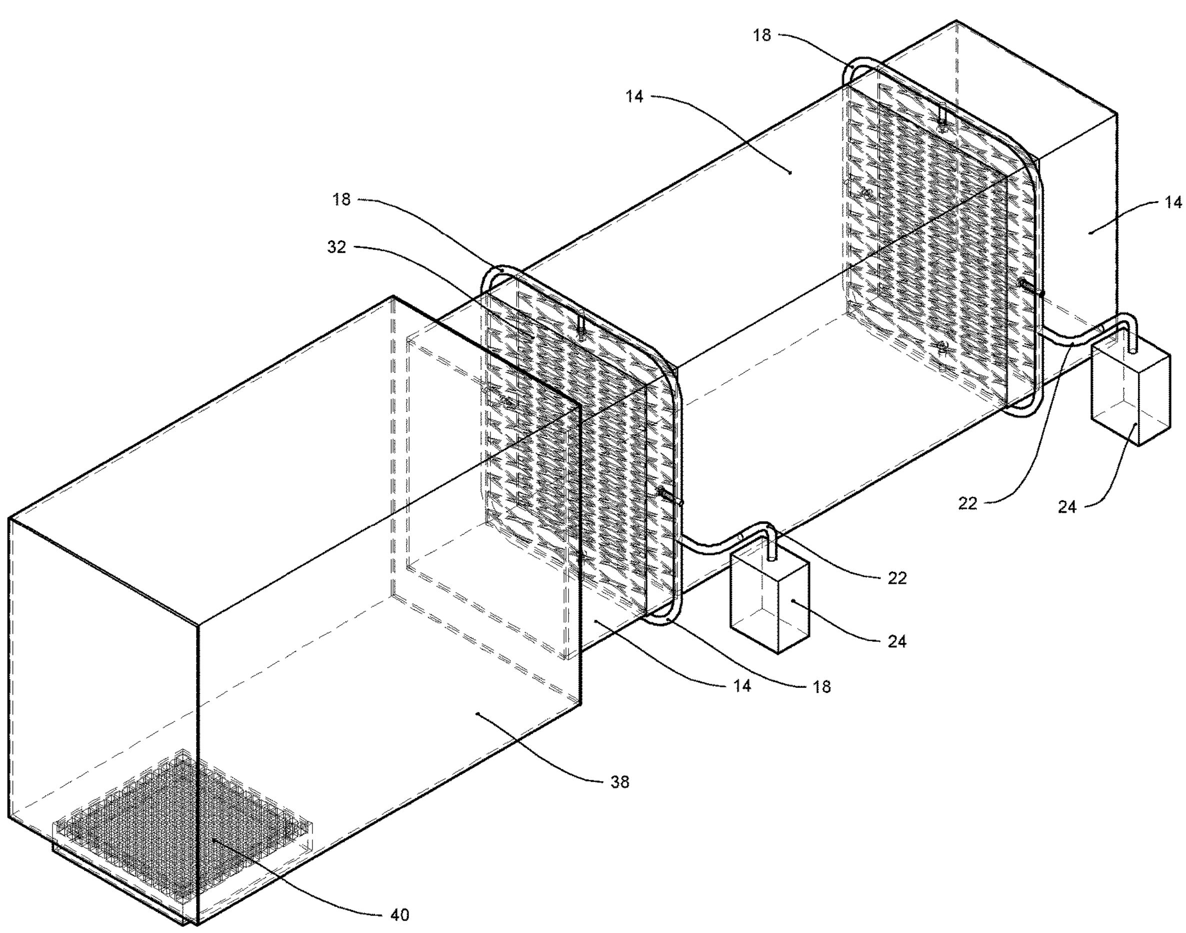
FIG. 8 is a perspective view of the air handler of the system with components shown in phantom.
Figure 9:
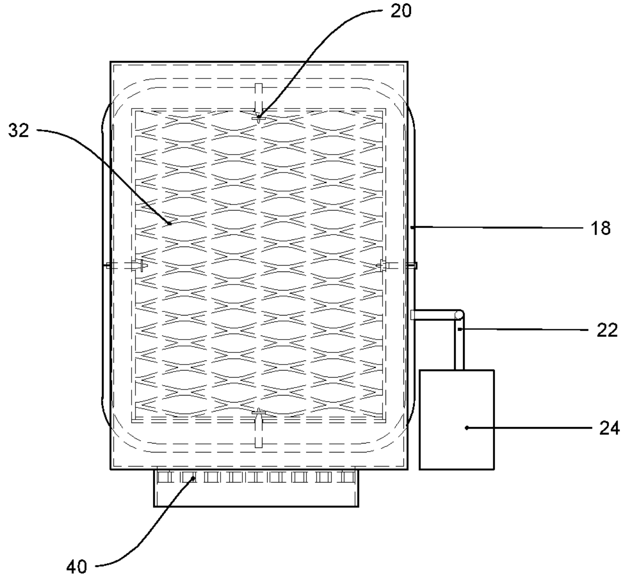
FIG. 9 is a front elevation view of the air handler of the system.
Figure 32:
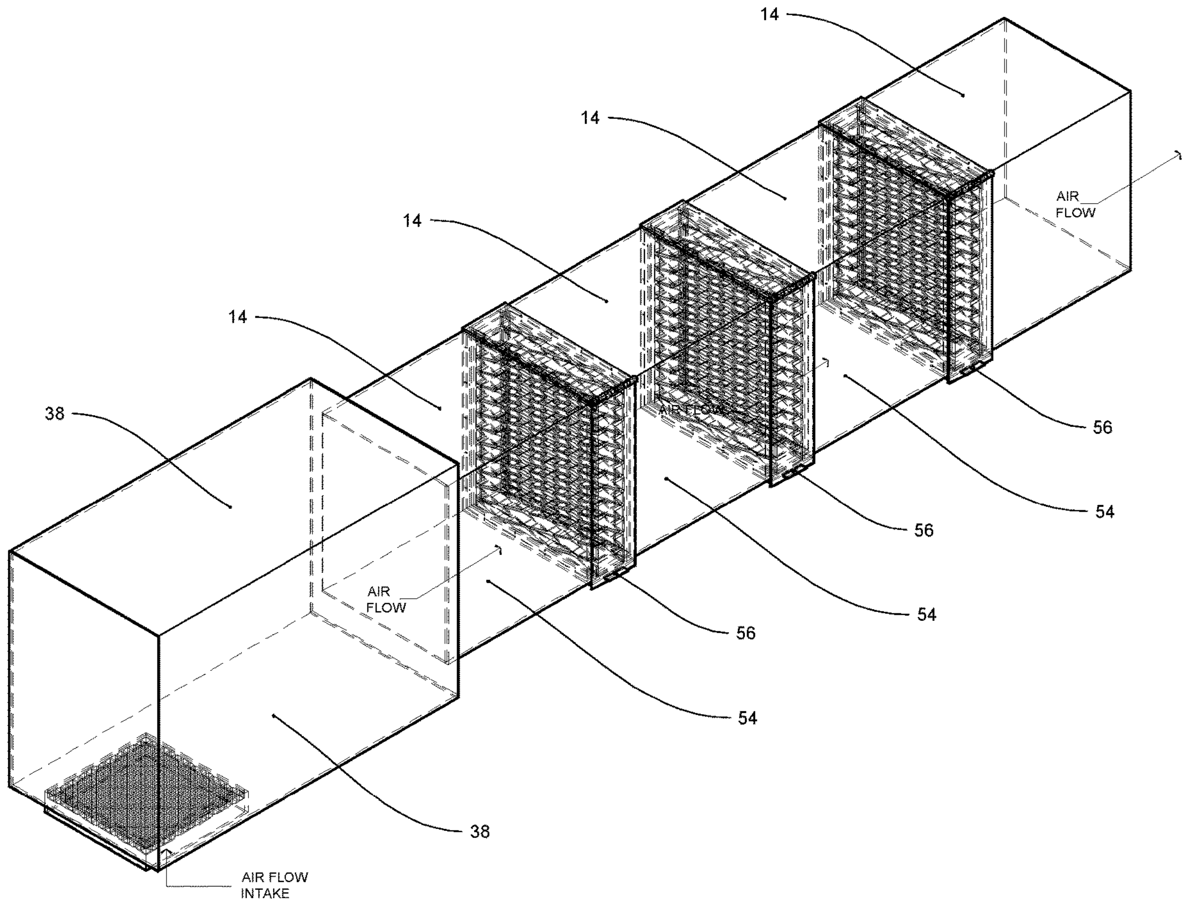
FIGS. 32 and 33 are a perspective views of an embodiments of the entire system including ultraviolet system, disinfecting system, and filter system.
Figure 33:
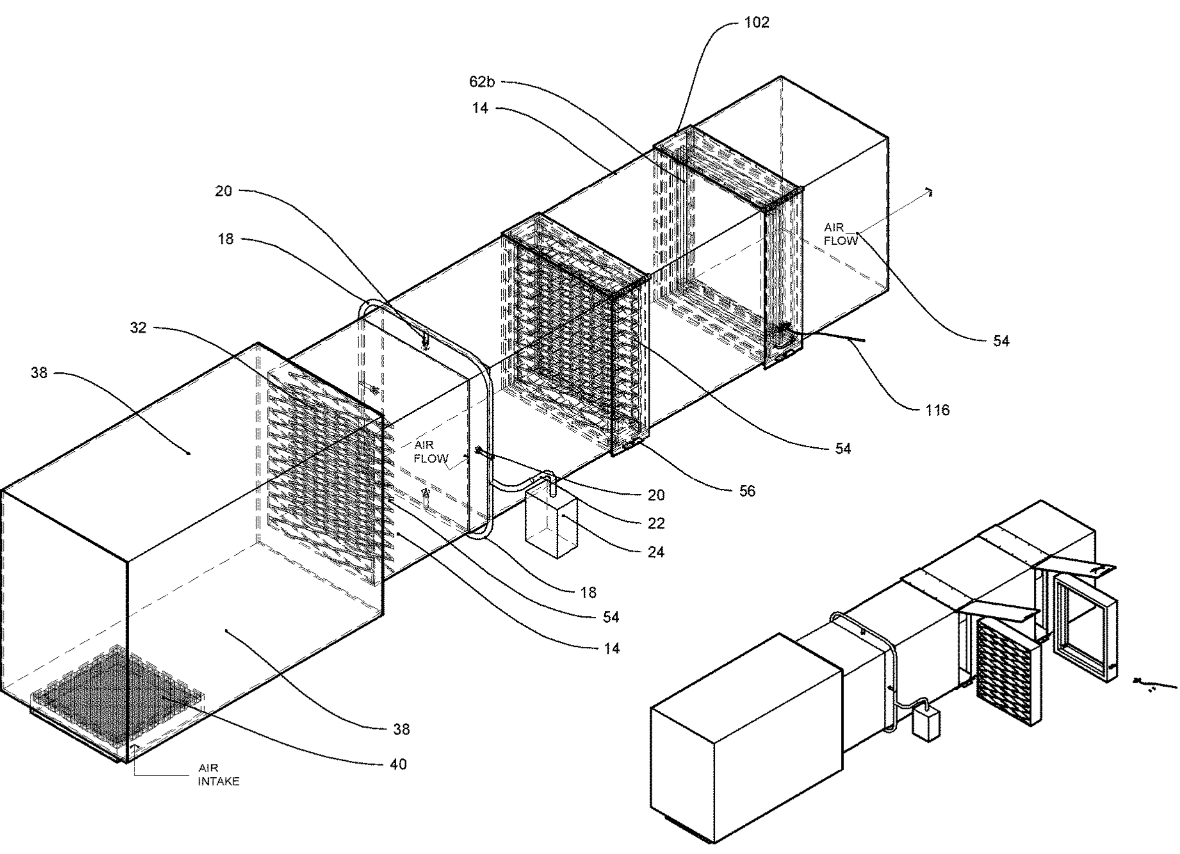

The system primarily operates with six stages, as may be seen in FIGS. 32 and 33. In the first stage 40, untreated air enters into the return 40 for the HVAC system 10. The air then travels through the second stage 15, which is an ultraviolet treatment area. At this point the air is mostly disinfected and then passes through the third stage 38, which is the air handler 38 of the system. After passing through the air handler 38, it is necessary to decontaminate any residual pathogens left in the air, which may have accumulated from surfaces in the HVAC system. The fourth stage 102 is an additional ultraviolet treatment area, as shown Primarily in FIGS. 25A-27D, and FIGS. 30A-31C. The fifth stage 35 is a disinfecting area, which can be either a spray or mist system 36 with disinfectant solution, shown primarily in FIGS. 1-15, or a solid filter 32, dipped in liquid disinfectant and left to dry, as shown primarily in FIGS. 6, 8, 16A-16C, 19A-19C, and 22A-24C. In some embodiments, both a liquid spray or mist system 36 and a dry solid filter 32 are used, as may be appreciated from FIG. 6. Once it passes through this disinfecting stage 35, the air passes to its final stage 13, flowing through the system supply 13.

Also shown in FIGS. 1-15 are the intake filter vent 26, vent frame 28, and vent grill 30, the disinfecting filter mounting frame 34, and air return filter.

Because HVAC systems in buildings may be complex, and replacing said systems could be an issue, this invention allows for an easy retrofit. Each component is easily adaptable for use with an existing system. For example, a cut in the ductwork can be made to allow the stainless steel frame 60*a* enclosing a filter 32 to be inserted, wherein the frame housing 62*a*/62*b* is contoured to match the profile of the existing ductwork 14. Once this frame 60*a* is inserted, the filters 32 can be interchanged, refreshed, or replaced as necessary. The filters 32 can also be systematically sprayed by spray nozzles 20, as may be seen in FIGS. 6 and 8, with disinfectant to continuously keep a layer of disinfecting material on said filter 32.

Figure 10:
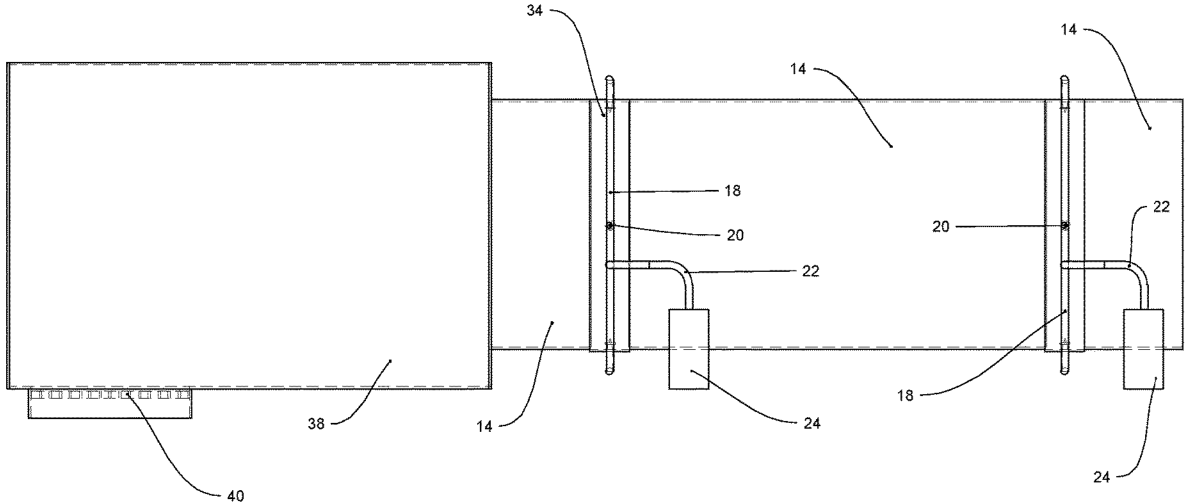
FIG. 10 is a side elevation of the air handler of the system.
Figure 11:
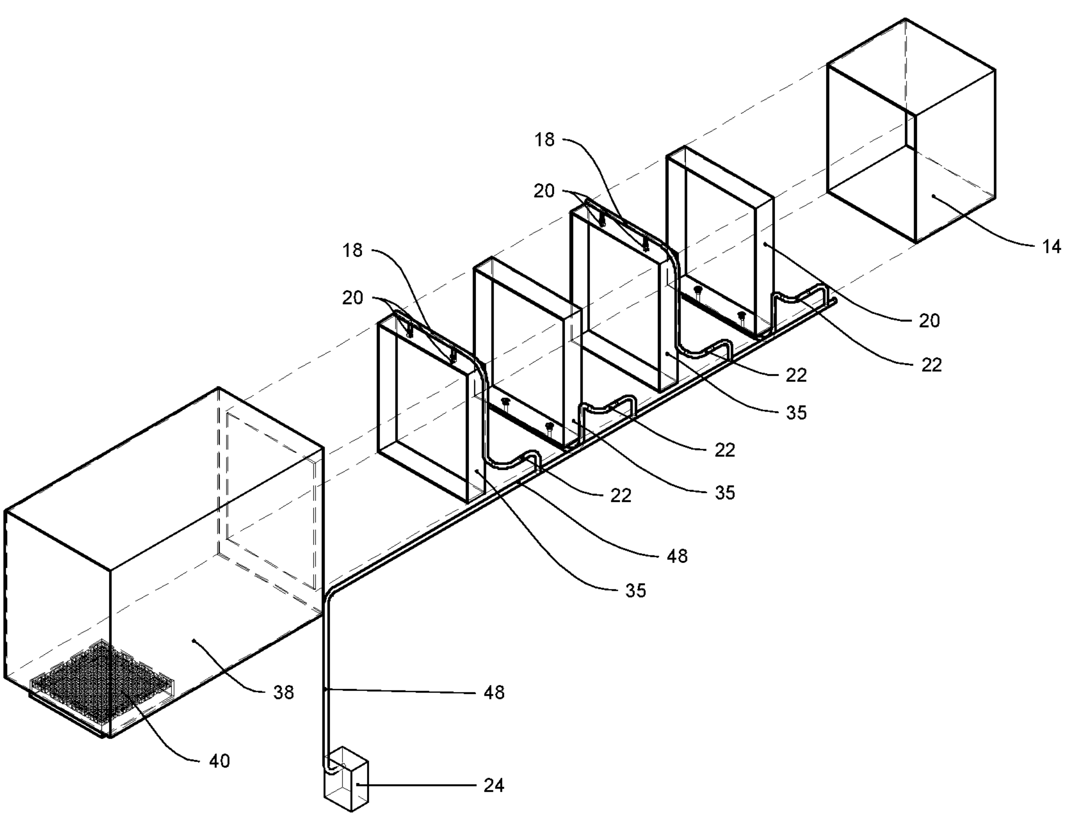
FIG. 11 is a perspective view of the air handler of the system with a centralized sanitizer system with satellite spray nozzles.
Figure 12:
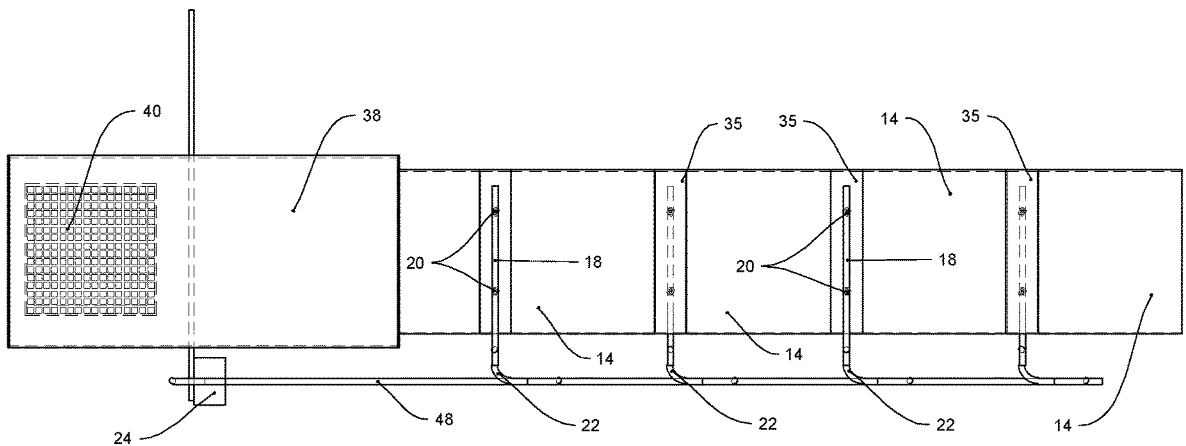
FIG. 12 is a top view of the air handler shown in FIG. 13, with vent shown in phantom.
Figure 13:
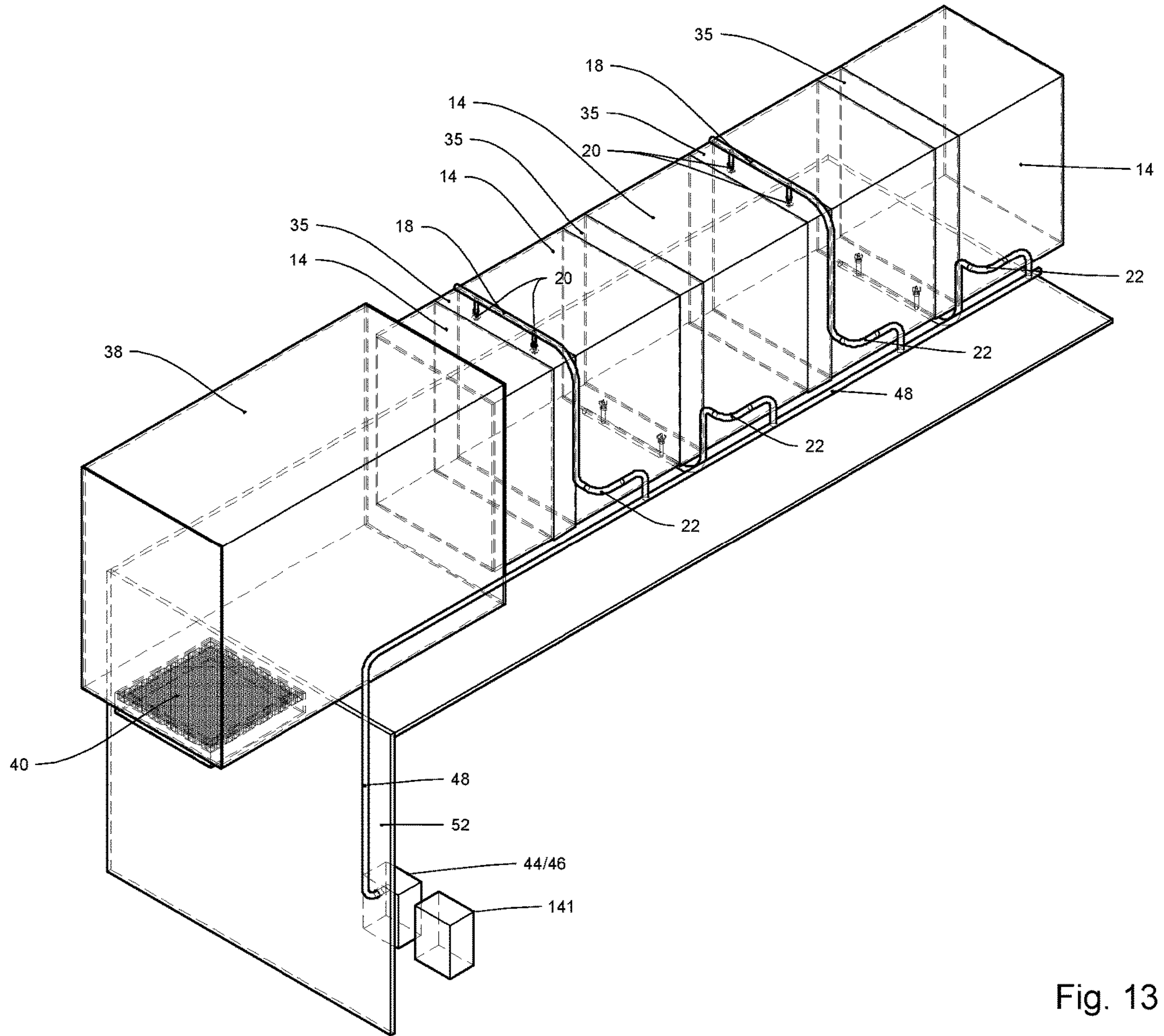
FIG. 13 is a perspective view of the air handler of the system shown in FIG. 11 with ductwork.
Figure 14:
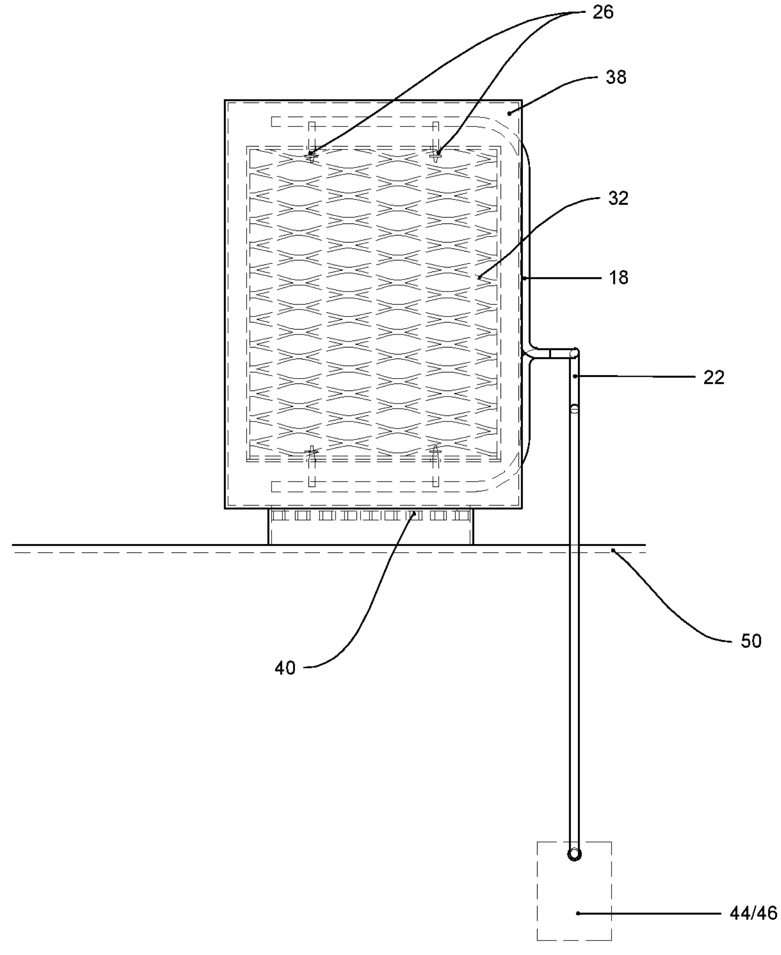
FIG. 14 is a front elevation view of the air handler system shown in FIG. 13, with filter shown in phantom.
Figure 15:
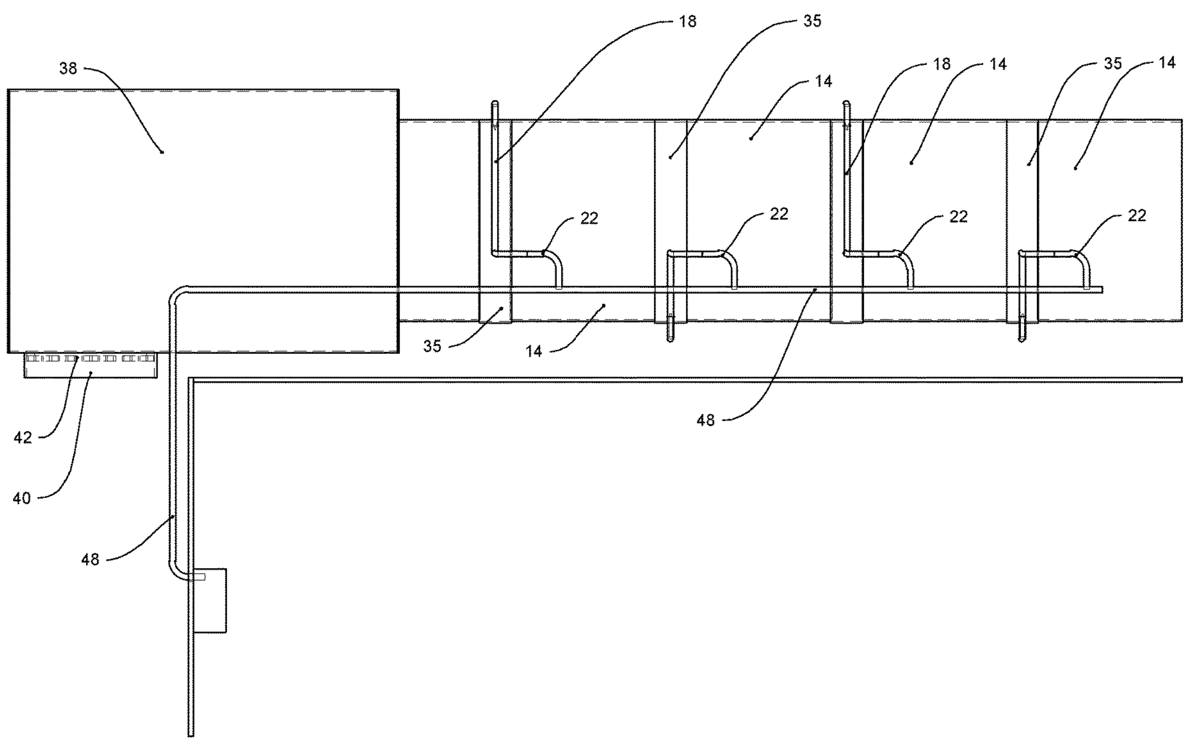
FIG. 15 is a side elevation view of the air handler system shown in FIG. 13.

Spray nozzles 20 are inserted into the ductwork 14. The hose 18/22 for the spray system nozzles 20 can be installed on the interior of existing AC ductwork 14, or on its exterior with penetrations 16 into the ducts 14 for inserting these nozzles 20. A rubber airtight sleeve is used when penetrating the duct 14 to provide an aperture 16 for the nozzle 20 spray system 36. The nozzles 20 may be pointed at the filters 32 to keep a continuous layer of disinfecting material on the filter 32, or may be positioned to create a spray or mist that decontaminates the air directly, as shown in FIGS. 10 and 11. A reservoir 24/44/46 can be located either locally near the spray nozzles 24 above a drop ceiling 50, as may be seen in FIGS. 6, 7, 8, and 10, or centrally contained in a reservoir 44 near the HVAC equipment in a utility closet, as shown in FIGS. 11-15. These reservoirs 24/44/46 are ideally refillable, however, there may be instances where the reservoirs 24/44/46 are prefilled replaceable containers that are swapped out when empty. Mechanical pumps will be used to inject disinfectant through the spray nozzle 20, and can similarly be centrally located in the HVAC utility closet, or a plurality can be spread out to key areas of the duct work, allowing targeted disinfecting with pumps being individually programmed or automated.

Also shown in FIGS. 11-17 are the wall 52, a path of airflow 54, a replaceable filter segment 56, and a duct cut 58.

Automation is a key element to this system. Prior to this invention, an occupant of an area needs to physically disinfect an area by using a spray bottle, but this does not monitor the current conditions. This system will ideally be used with a programmable interface that is wirelessly enabled, such as Wi-Fi or Bluetooth enabled. A control module may be set, like a timer, or may be programmed to automate the system based on time of day, day of the week, based on occupancy, or randomized for efficiency. The system allows for both automation and control, wherein the automated system will monitor current conditions and initiate disinfecting as necessary, whereas control would allow a user to initiate the program whenever said user feels it necessary to activate the disinfecting system. This operability allows for maximum flexibility for a controlled disinfecting.

Further, ultraviolet lamps 108 are included for disinfecting. Similar to inserting a filter 32, a segment of ducting is cut from the existing ductwork 14. Therein, a stainless steel frame 62*b* is inserted into a frame housing 64*b*, formed to match the contour of the duct 14, as may be seen in FIGS. 27A-31C. There, interchangeable ultraviolet lamps 108 mounted to a steel frame 110 may be inserted. The lamps 108 can be calibrated for the intensity needed to kill any pathogens, or reduce them by a desired number. The system can include a single bulb 114, or a plurality of bulbs 108 as necessary. As may be seen in FIGS. 30A-30D, an array of ultraviolet lights 108 are mounted to the steel frame 110. Each light 114 in the array of ultraviolet lights contains a bulb 114, and glass covering 112.

This system may have multiple configurations, or a combination of some or all configurations. A first configuration includes a metal frame 60*a* with removable filter 32 and sanitary injection HVAC feed 18 with spray nozzles 20. In the first configuration, the existing HVAC is separated at several points along the trunk line of the A/C duct 14. A frame 60*a* and frame housing 62*a* are inserted between two ducts 14. On the frame 60*a* there is a protrusion that is trained on the center of the A/C duct 14. At the end of the protrusion is the spray nozzle 20. A hose 18 connects the stem of the nozzle 20 to a supply hose 22/48 to a reservoir 24/44/46 of disinfectant. At timed intervals, a spray will be emitted directly into the main trunk line to sanitize the air circulating through the ducts 14. The filter 32 will be removed and replaced as needed. For sensitive areas the filter will require replacement more often. With several installments throughout the A/C ductwork, the sprays can either be simultaneously or programmed to work independent of each other.

In a second configuration, with multiple penetrations 16 throughout ductwork 14, a frame-less installation is used with multiple penetration points 16 along the A/C duct system. These penetrations 16 will be sized for spray nozzles 20 spaced out periodically through A/C ductwork 14. The nozzles will be emitting the disinfectant starting with higher concentrations at the beginning of the line and then reducing concentrations down the line. This system can be programmed to release at once or systematically down the trunk of the duct. The purpose of the spray is to mix with contaminated air, purifying it and then supplying it back to the building.

Figures 16A, 16B:
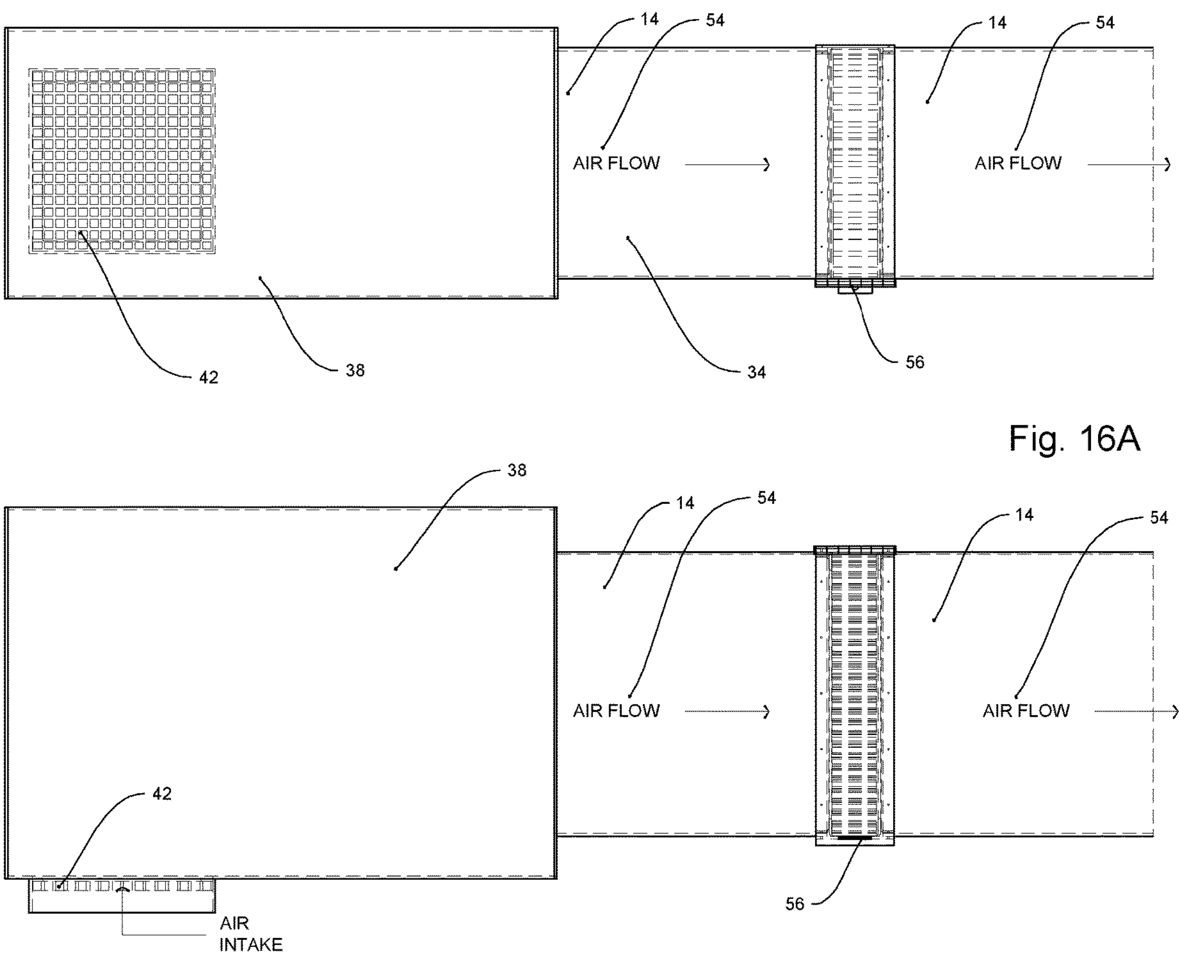
FIG. 16A is a top view of the replaceable air filter system.
FIG. 16B is a side view of the replaceable air filter system.
Figure 16C:
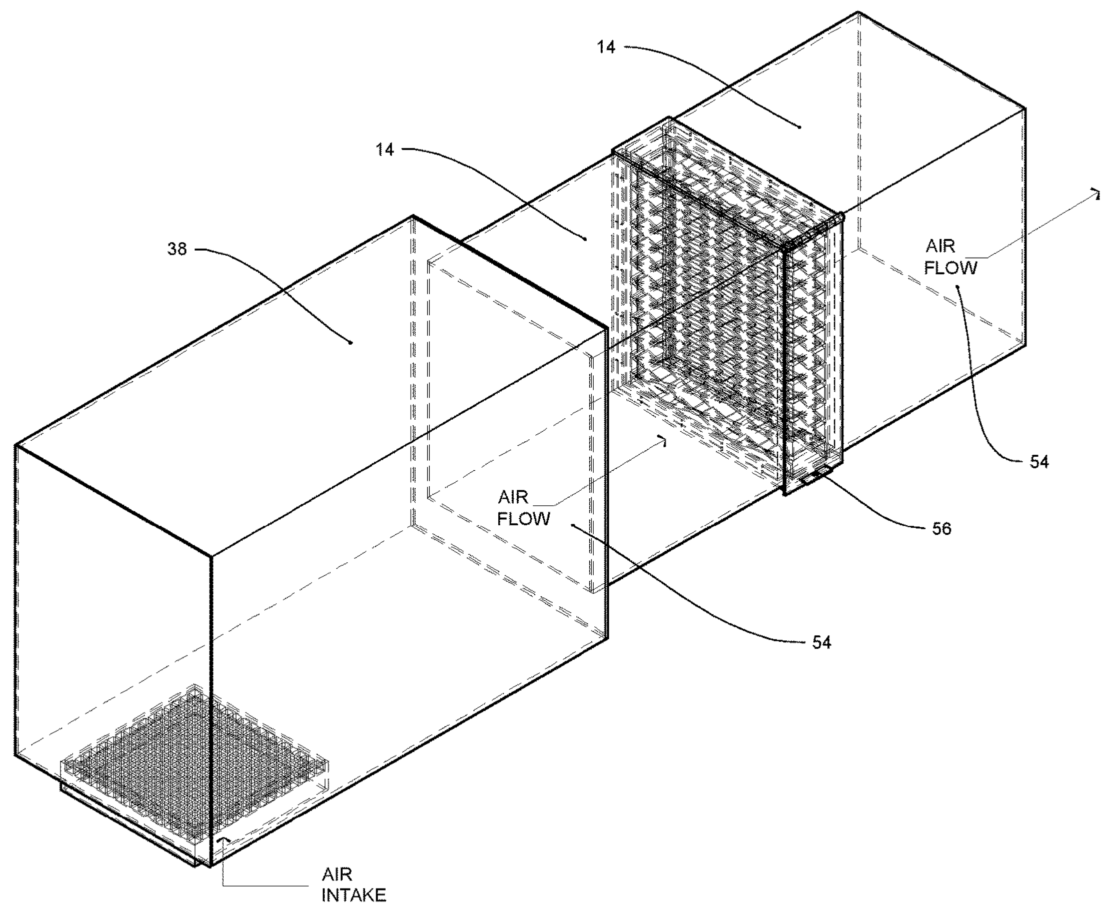
FIG. 16C is a perspective view of the replaceable air filter system.
Figure 17:
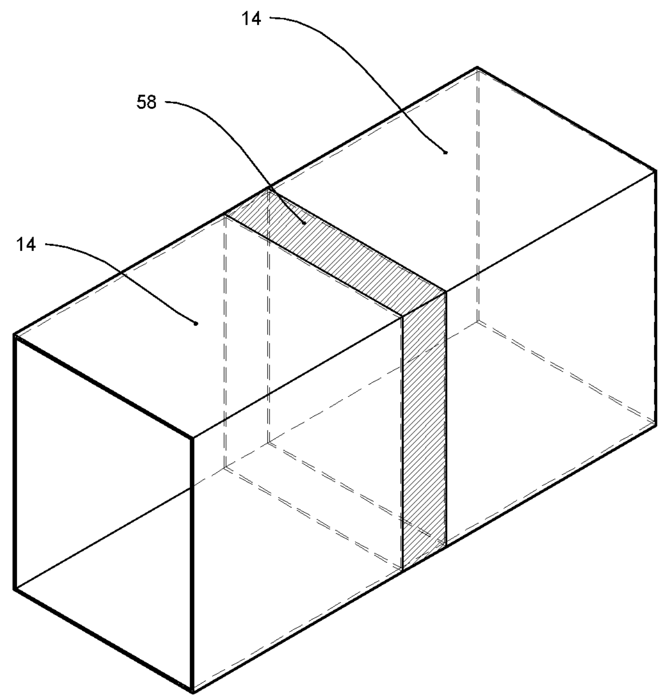
FIG. 17 is a perspective view of the duct cut for the replaceable air filter system.
Figures 18A, 18B:
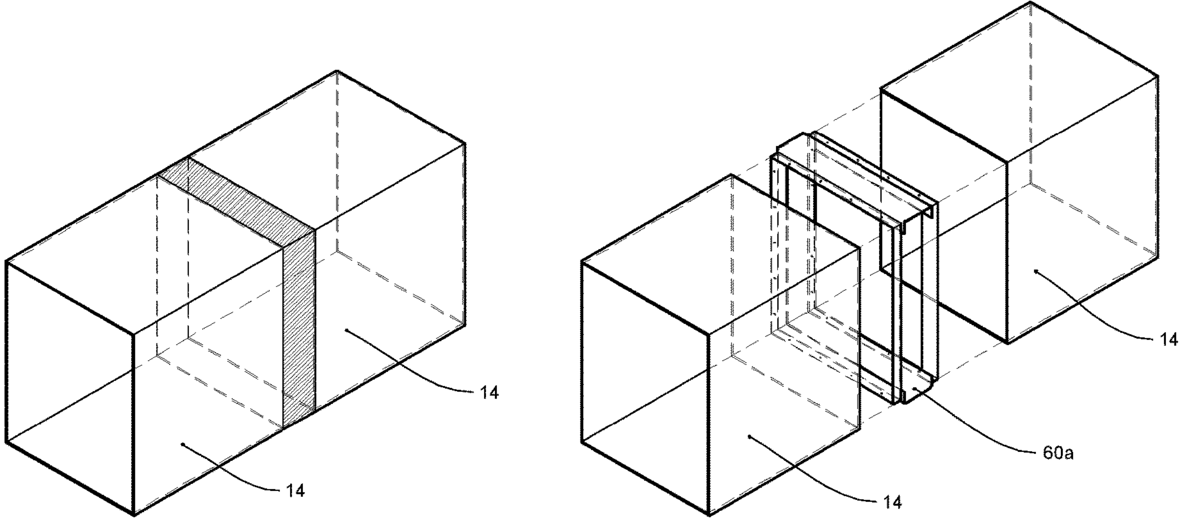
FIG. 18A is a perspective view of the mounting for the filter frame for the replaceable air filter system.
FIG. 18B is a perspective view of the mounted filter frame for the replaceable air filter system.
Figure 18C:
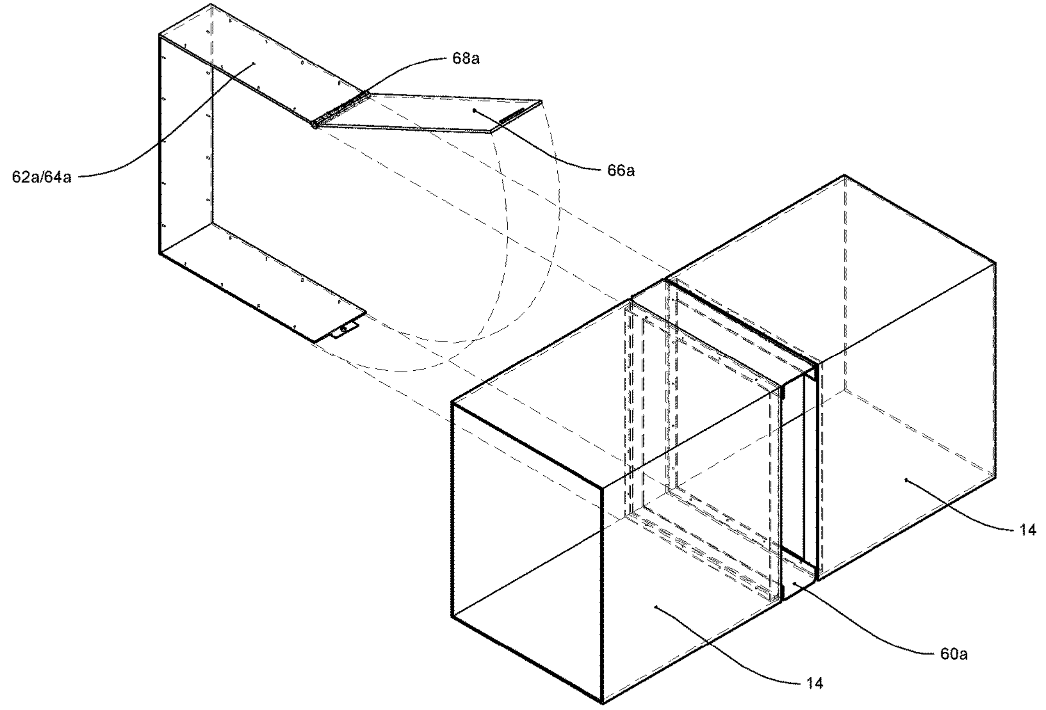
FIG. 18C is a perspective view of the disengaged mount clamp and door for the replaceable filter system.
Figures 18D, 19A:
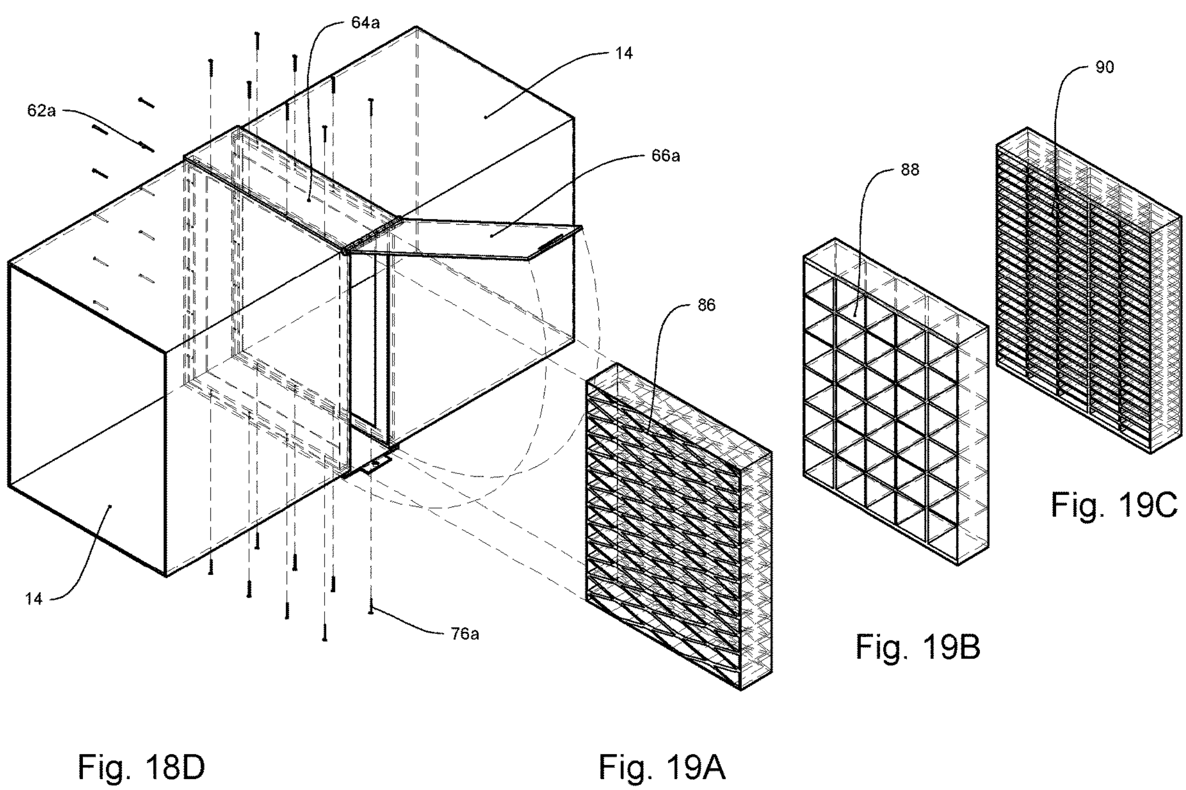
FIG. 18D is a perspective view of the engaged mount clamp and door for the replaceable filter system.
FIG. 19A is an embodiment of a filter used with the replaceable filter system shown in FIG. 18D.
Figures 20A, 20B, 20C, 20D, 20E:
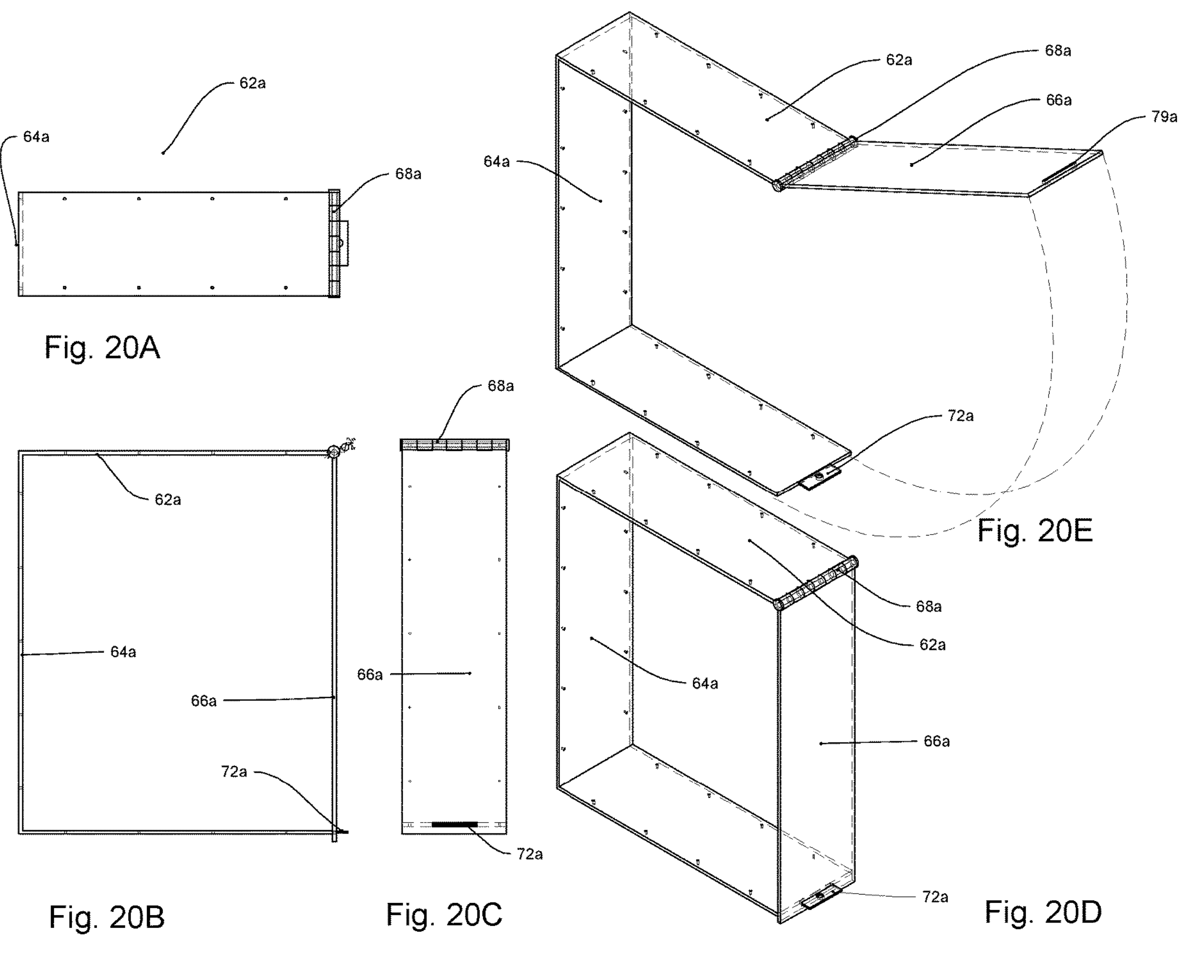
FIG. 20A is a top view of the mount clamp and door shown in FIG. 18C.
FIG. 20B is a front view of the mount clamp and door shown in FIG. 18C.
FIG. 20C is a side view of the mount clamp and door shown in FIG. 18C.
FIG. 20D is a perspective view of the mount clamp and door shown in FIG. 18C.
FIG. 20E is a perspective view of the mount clamp and door shown in FIG. 18C, with door shown open.
Figures 21A, 21B, 21C, 21D, 21E:
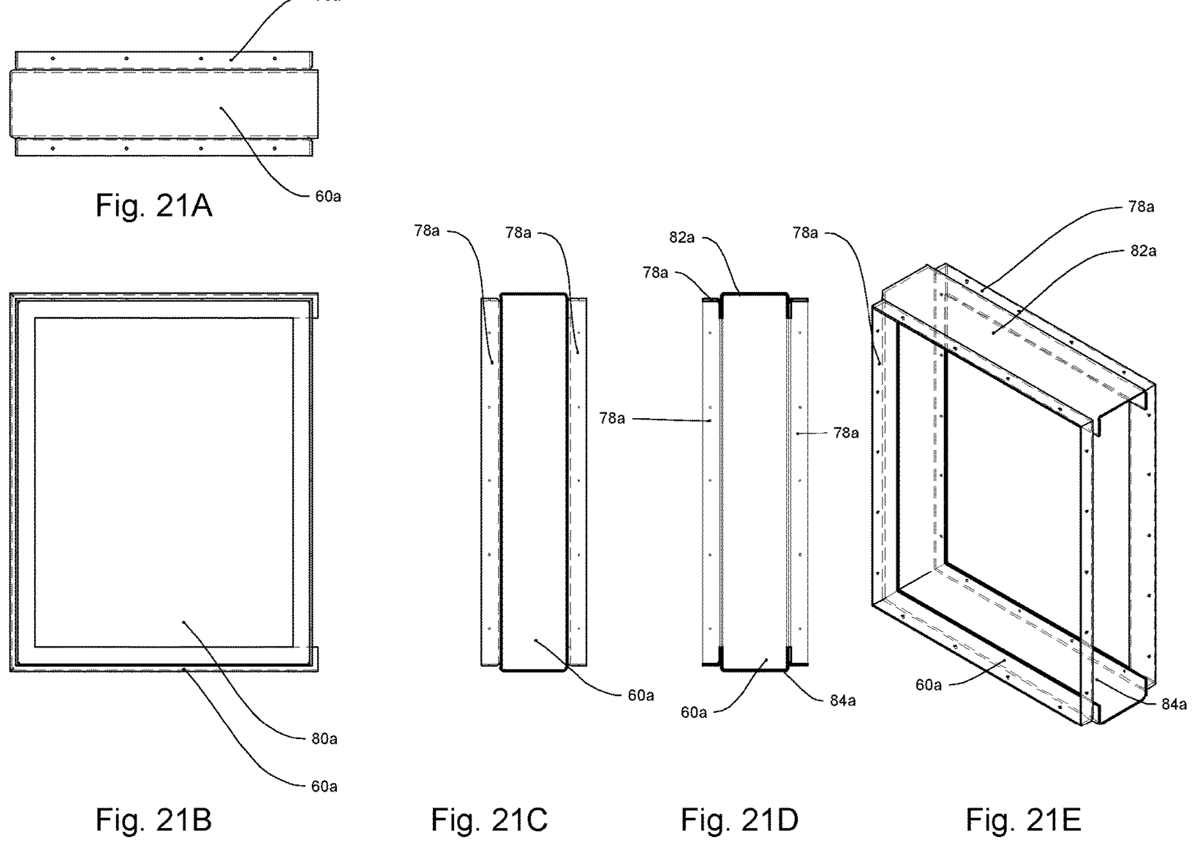
FIG. 21A is a top view of the filter frame shown in FIG. 18A
FIG. 21B is a front view of the filter frame shown in FIG. 18A
FIG. 21C is a side view of the filter frame shown in FIG. 18A
FIG. 21D is a section view of the filter frame shown in FIG. 18A, taken from A-A shown in FIG. 21B.
FIG. 21E is a perspective view of the filter frame shown in FIG. 18A
Figures 25A, 25B:
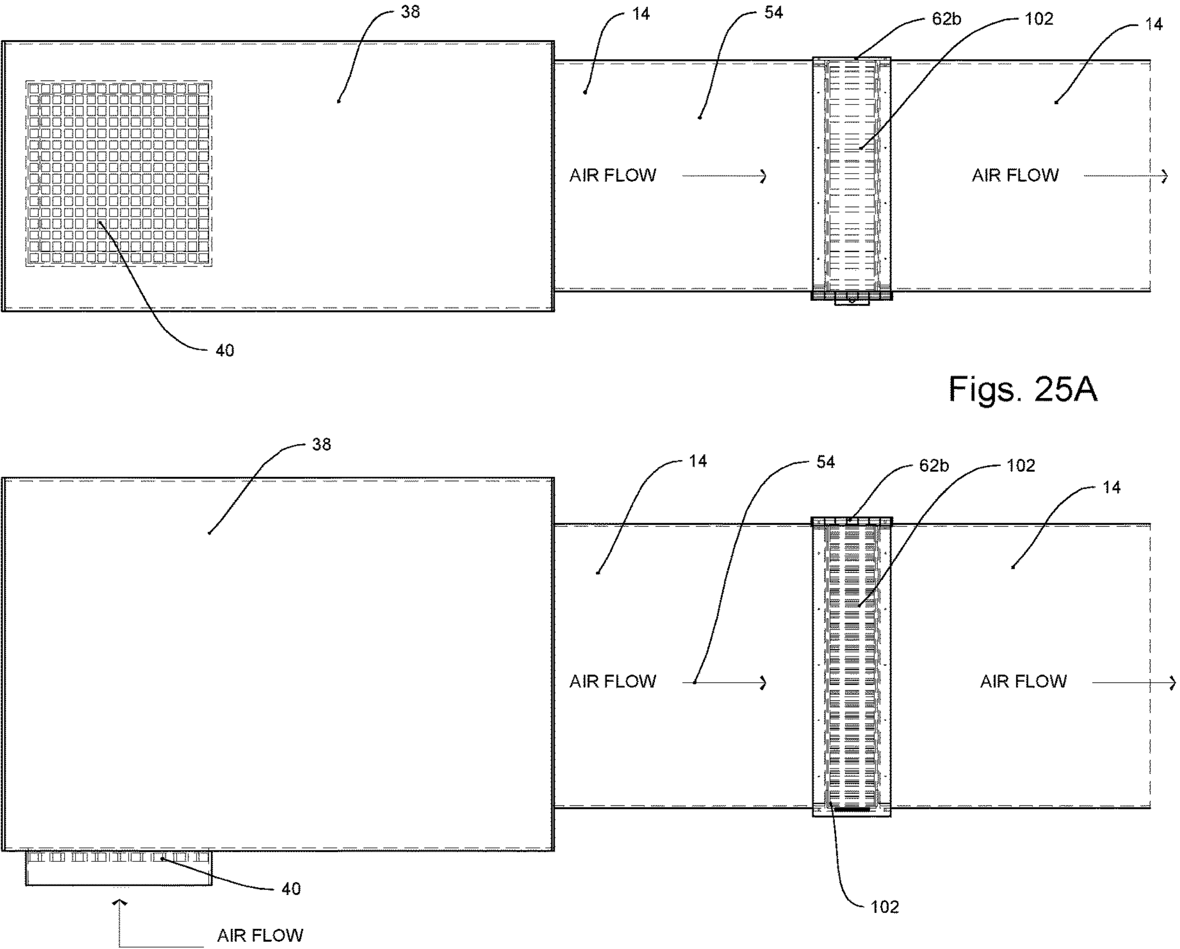
FIG. 25A is a top view of the interchangeable ultraviolet system.
FIG. 25B is a side view of the interchangeable ultraviolet system.
Figure 25C:
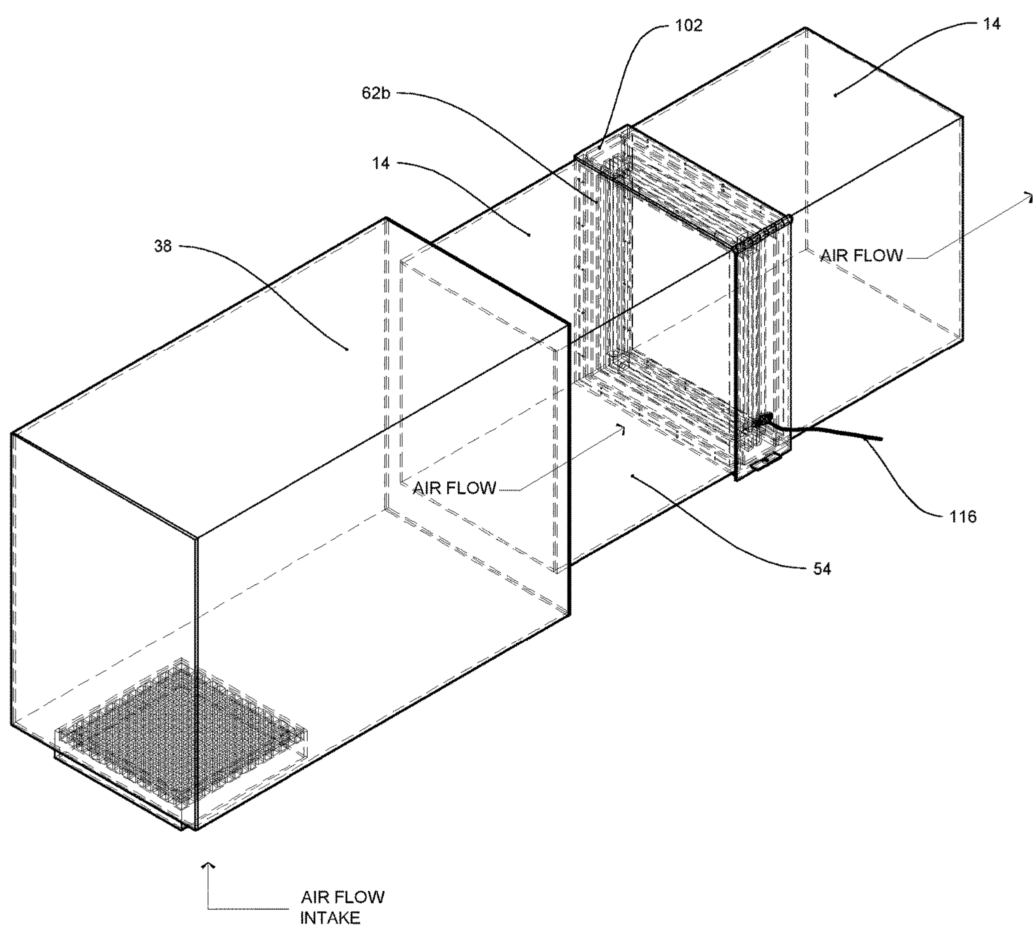
FIG. 25C is a perspective view of the interchangeable ultraviolet system.
Figure 26:
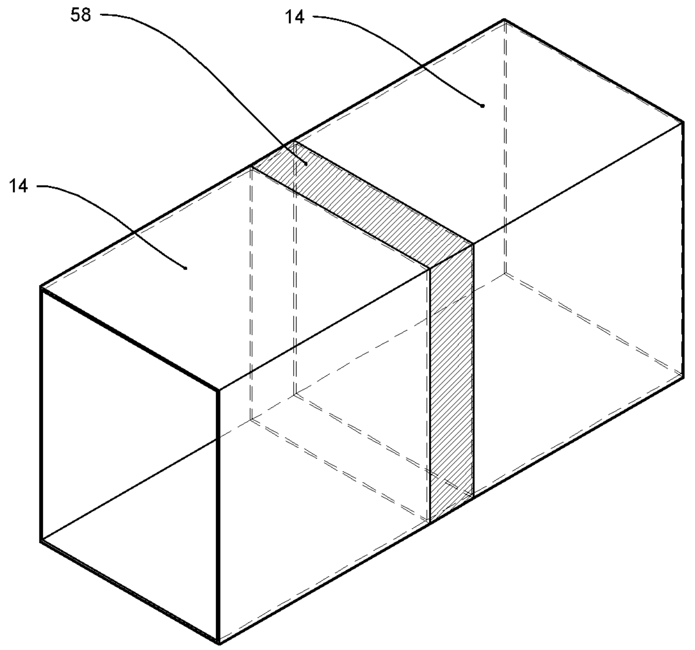
FIG. 26 is a perspective view of the duct cut for the interchangeable ultraviolet system.
Figures 27A, 27B:
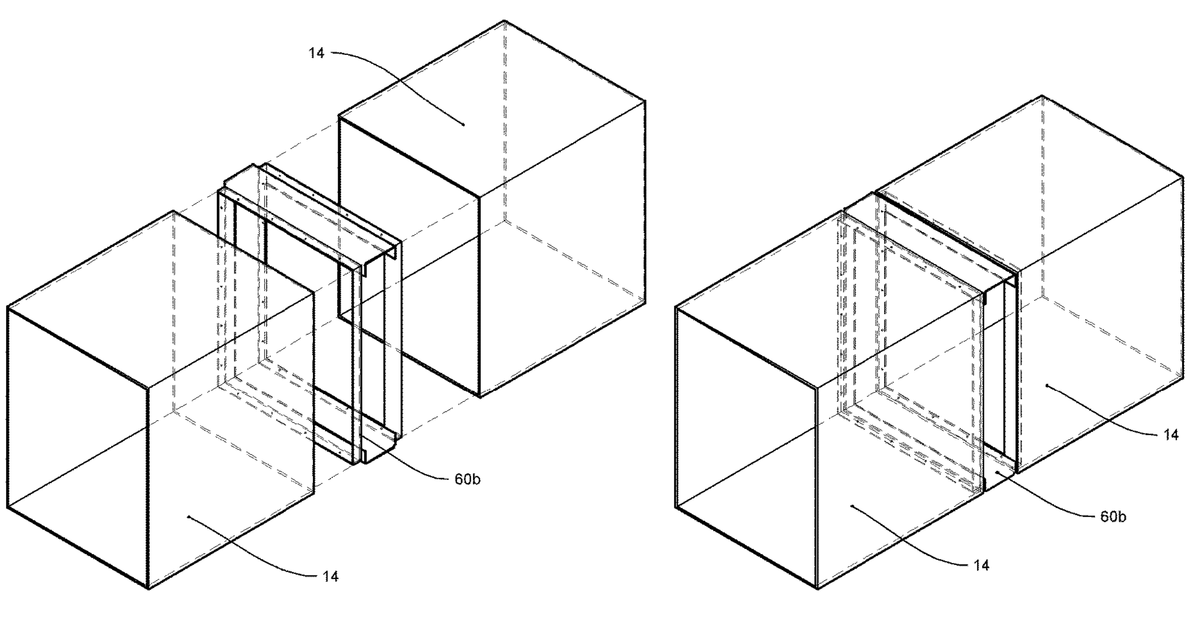
FIG. 27A is a perspective view of the mounting for the ultraviolet frame for the interchangeable ultraviolet system.
FIG. 27B is a perspective view of the mounted ultraviolet frame for the interchangeable ultraviolet system.
Figure 27C:
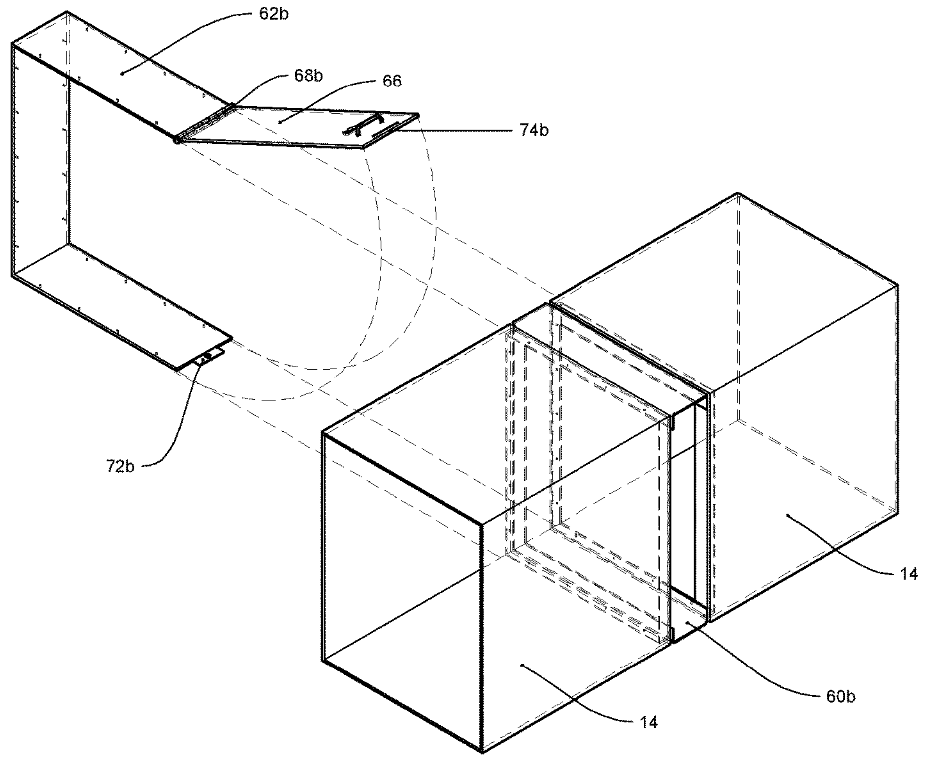
FIG. 27C is a perspective view of the disengaged mount clamp and door for the interchangeable ultraviolet system.
Figures 27D, 27E:
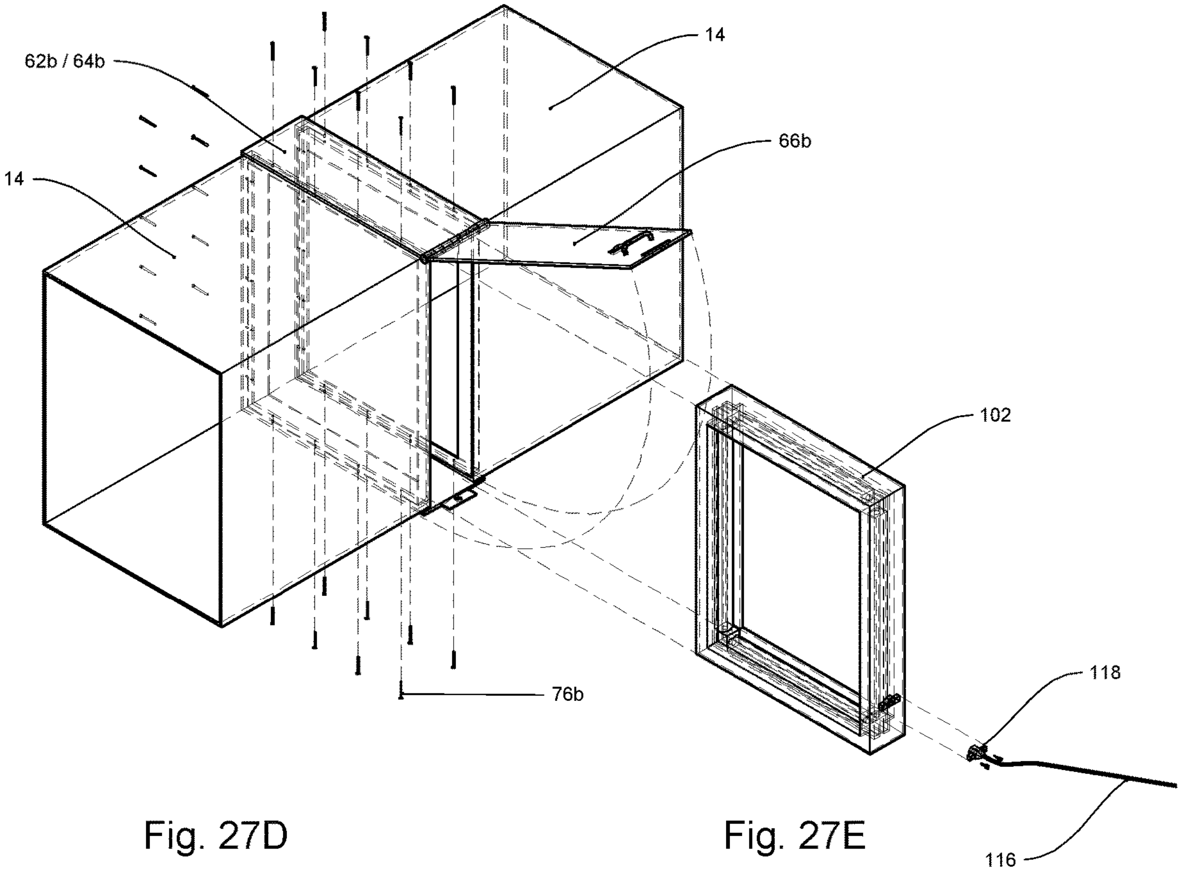
FIG. 27D is a perspective view of the engaged mount clamp and door for the interchangeable ultraviolet system.
FIG. 27E is a perspective view of the interchangeable ultraviolet system used with the mounting frame shown in FIG. 27D.
Figures 28A, 28B, 28C, 28D, 28E:
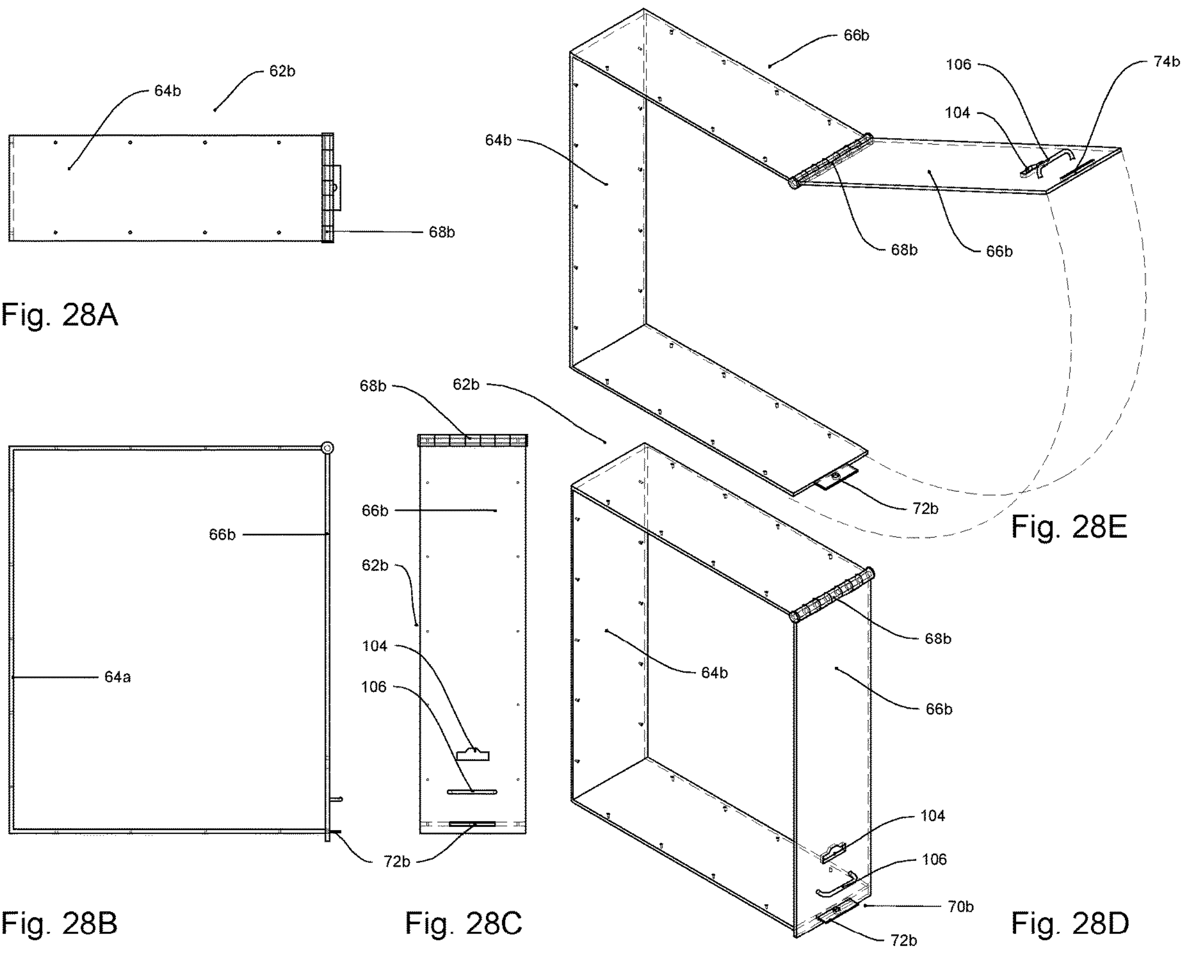
FIG. 28A is a top view of the mount clamp and door shown in FIG. 27C.
FIG. 28B is a front view of the mount clamp and door shown in FIG. 27C.
FIG. 28C is a side view of the mount clamp and door shown in FIG. 27C.
FIG. 28D is a perspective view of the mount clamp and door shown in FIG. 27C.
FIG. 28E is a perspective view of the mount clamp and door shown in FIG. 27C, with door shown open.
Figures 29A, 29B, 29C, 29D, 29E:
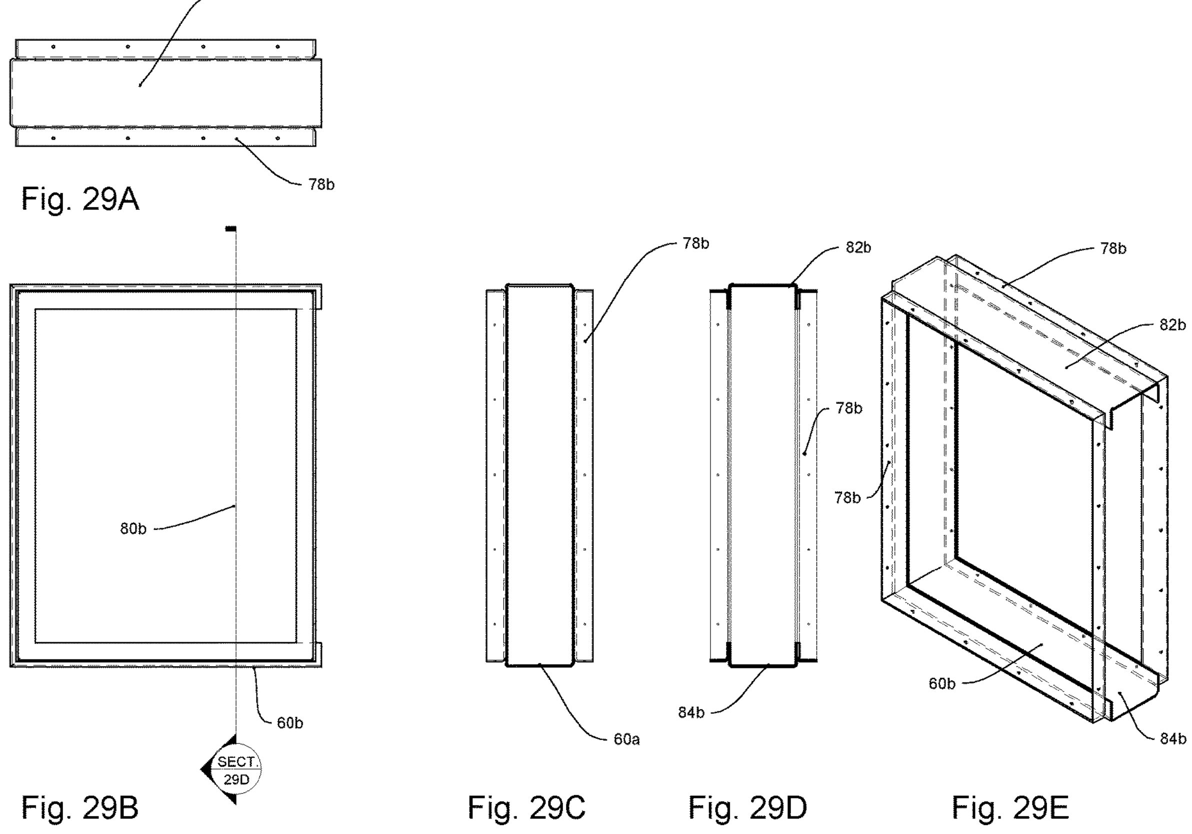
FIG. 29A is a top view of the ultraviolet frame shown in FIG. 27A
FIG. 29B is a front view of the ultraviolet frame shown in FIG. 27A
FIG. 29C is a side view of the ultraviolet frame shown in FIG. 27A
FIG. 29D is a section view of the ultraviolet frame shown in FIG. 27A, taken from A-A shown in FIG. 29B.
FIG. 29E is a perspective view of the ultraviolet frame shown in FIG. 27A.
Figures 30A, 30B, 30C, 30D:
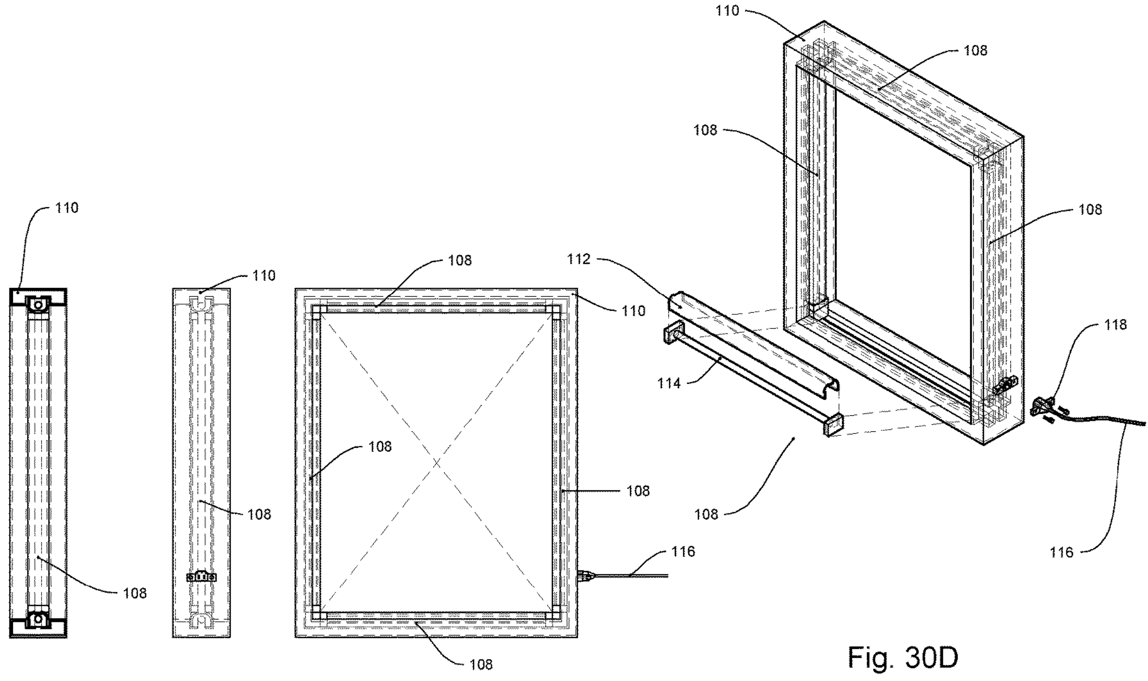
FIG. 30A is a section view of the replaceable ultraviolet system.
FIG. 30B is a side view of the replaceable ultraviolet system.
FIG. 30C is a front view of the replaceable ultraviolet system.
FIG. 30D is a perspective view of the replaceable ultraviolet system.
Figure 31A:
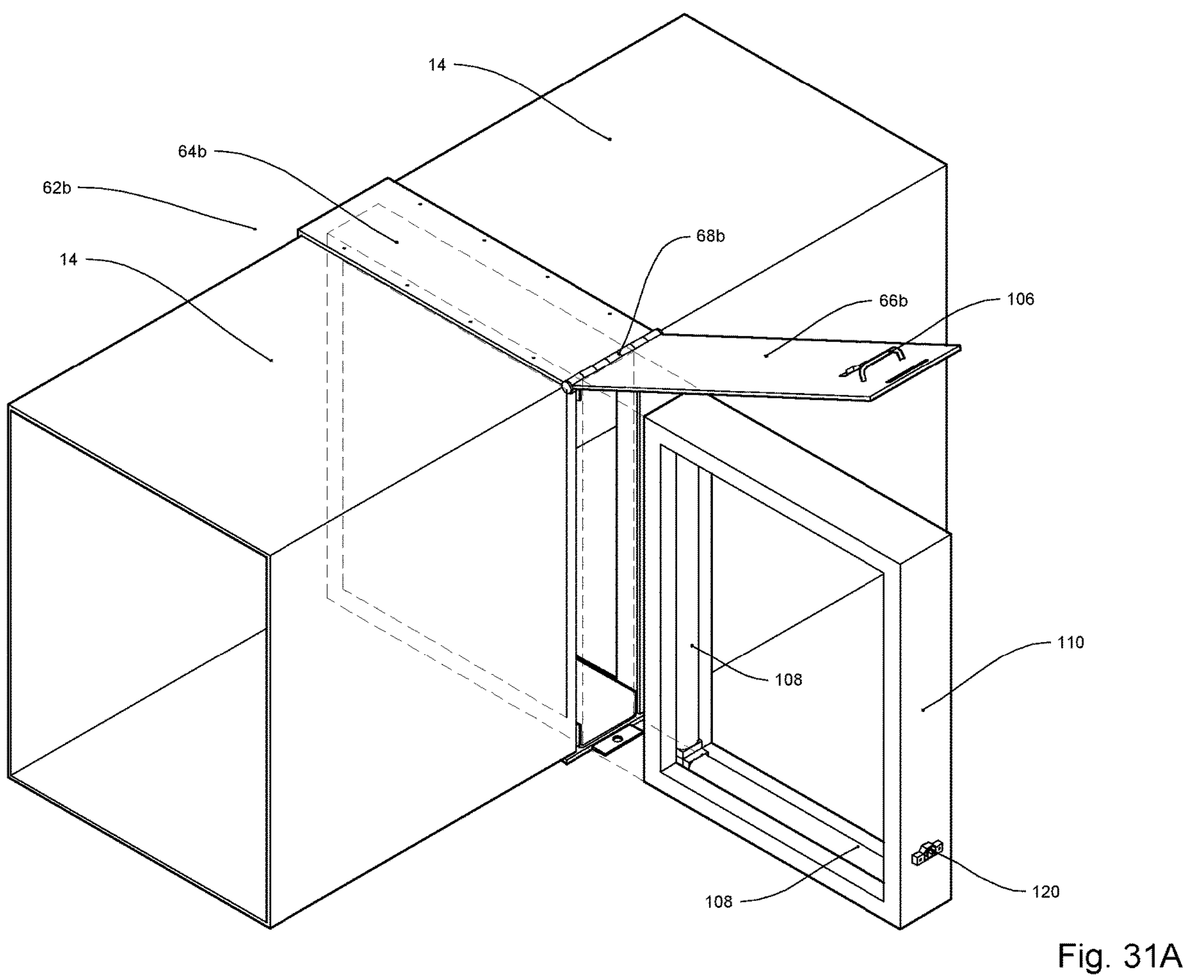
FIG. 31A is a perspective view of the ultraviolet system similar to FIGS. 27D and 27E.
Figures 31B, 31C:
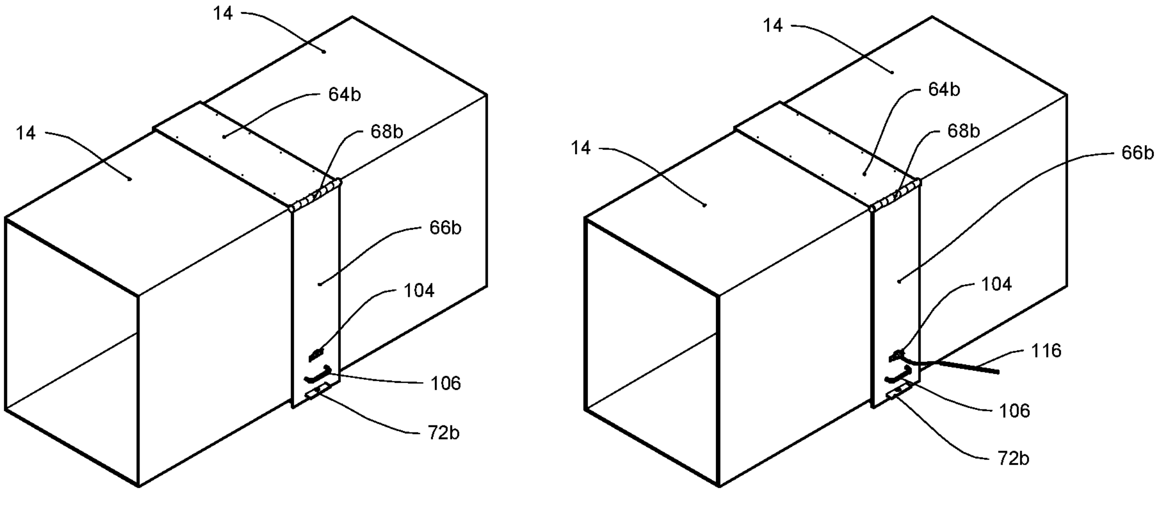
FIG. 31B is a perspective view of the ultraviolet system of FIG. 31A with the door securely closed.
FIG. 31C is a perspective view of the ultraviolet system as shown in FIG. 31B with the attached power cord.

In a third system, shown primarily in FIGS. 16A-16C, and also shown in FIGS. 17-26, a filter 32 with three-dimensional webbing 92, the actual filter 32 will look more like graphing paper, just extended in the z axis to provide depth and more importantly, increased surface area to collect pathogens circulating throughout the ducts. This may be seen primarily in FIGS. 19A-19C and 22A-24C. The filter 32 will be dipped into an antimicrobial solution and then dried. Once installed the filter 32 will catch traveling pathogens. The filter 32 will require replacement periodically. The filter 32 can be installed in multiple locations to enhance its functionality. For example, placing one filter 32 inside the condenser and one at the supply vent 13*a*, the air can be filtered twice before entering a room.

In an embodiment of the system 10, the invention provides for a system for disinfecting air circulated in an HVAC system. The system includes a multi-phase system, wherein the multi-phase system comprises at least six segments, with at least one segment representing each of at lease one air intake 12, at least one air handler 38, and at least one connecting ductwork 14.

The system also includes an arrangement of the at least six segments that correlates to six phases. Phase 1 is the air return 40 of an HVAC system; phase 2 is the plurality of ultraviolet lights 114 including an ultraviolet light array 108 before the air handler 38. The ultraviolet light array 108 comprises at least one ultraviolet light 114 in the plurality of ultraviolet lights 108. Phase 3 is the air handler 38. Phase 4 is a second ultraviolet array 108 comprising at least one ultraviolet light 114 in the plurality of ultraviolet lights 108 in the supply ductwork 14 after the air handler 38. Phase 5 is the airborne disinfecting system 36/32, and phase 6 is an air supply 13 of an HVAC system. The at least one connecting ductwork 14 is further defined as ductwork 14 connecting each of the six phases.

The system has at least one interchangeable filter 32, wherein each filter 32 in the at least one interchangeable filter 32 is an elongate three-dimensional grid 92 with a series of openings 94/98 to allow circulated are to flow over the air filter's elongate surfaces 96. The interchangeable filter is pre-dipped in a disinfecting solution, which is allowed to dry on the surfaces 96 of the interchangeable filter 32 to thereby kill any pathogen that may come in contact with the surfaces 96. The interchangeable filter 32 is located in a filter housing 62*a*, wherein the filter housing 62*a* connects two segments of the ductwork 14 and the filter housing 62*a* is contoured to align with perimeter dimensions of the ductwork 14. Perimeter dimensions mean that the filter housing has the same width and height as the ductwork 14 so that the edges meet flush.

Further, the filter housing 62*a* defining a four-walled metallic segment 62*a*, as shown in FIGS. 20A-20D with openings correlating to each of the two segments of ductwork 14. A closeable opening is created for insertion of the filter 32 therein created by a hinge 68*a* moveably coupling one wall 64*a* of the four-walled metallic segment 62*a* thereby creating a hinged flap 66*a*. Once the flap 66*a* is closed, the flap 66*a* seals an inside airflow channel 67 between each duct segment 14 connected by the four-walled metallic segment 62*a*.

Also shown in FIGS. 18A-21E are the door locking engagement mechanism 70*a* made of a flange with aperture 72*a* and an opening for the flange with the aperture 74*a*. Filter frame screws 76*a* are shown to provide securement of the filter frame 60*a*. Filter frame mounting flange 78*a* allows the filter frame 60*a* to mount within the ductwork 14 and filter frame housing 62*a*. Each frame 60*a* contains an opening 80*a* that correlates to the opening on the filter frame housing, and thereby allows passage of airflow through the ducts 14 and filter frame 60*a*. In addition, for structural support in guiding a filter 32 in each filter frame 60*a*, the filter frame 60*a* includes an inverted U-shaped channel 82*a* on top portion of the frame 60*a* and a U-shaped channel 84*a* on a bottom portion of said filter frame 60*a*. These channels 82*a*/84*a* guide the filter 32 during insertion.

In addition, FIGS. 22A-24C show a first embodiment filter 86, a second embodiment filter 88, and a third embodiment filter 90, each having individual cells 92 with an opening 98 and an exit 100.

The surfaces 96 of these interchangeable filters 32 are periodically sprayed with a disinfecting solution expelled through the nozzles 20 of the disinfecting system 36. This disinfectant solution thereby kills any pathogen that may come in contact with the surfaces 96 of the interchangeable filter 32.

Similarly, the housing 62*b* of the ultraviolet segment 108 resembles the housing 62*a* of the filter 32 segment. This is so filters 32 and ultraviolet arrays 108 may be swapped out as needed. Keep in mind, however, that ultraviolet arrays 108 should not be swapped into an area that is in direct relation to spray nozzles 20. As may be appreciated in FIGS. 25A-31C, the ultraviolet filter segment also contains a frame 60*b*, frame housing 62*b*, housing structural frame 64*b*, flap 66*b*, hinge 68*b*, flap locking engagement mechanism 70*b*, flange with aperture 72*b*, opening for flange in flap 74*b*, frame screws 76*b*, mounting flange 78*b*, opening 80*b*, upper channel 82*b*, and lower channel 84*b*. Also shown is a power aperture 104 in the flap 66*b*, a flap handle 106, electrical feed 116, electrical feed screws 118, and an electrical inlet 120.

In some embodiments, the at least one spray nozzle 20 is mounted inside the connecting duct 14. In other embodiments, the at least one spray nozzle 20 is mounted outside the connecting duct 14 and extends through an aperture 16 of the connecting duct 14.

The airborne disinfecting system further includes a spray ring 18 defined by a perimeter hose 18 connecting the supply hose 22/48 to the at least one spray nozzle 20, wherein a plurality of spray nozzles 22 are mounted along the spray ring 18. The spray ring 18 may form a continuous loop surrounding the outer surface of the ductwork 14, and the spray nozzles 20 connected to the spray ring 18 extend through the apertures 16 in the duct work 14. These apertures 16 are then sealed by rubber gaskets 20*a*.

The system also has a plurality of ultraviolet lights 114, and an airborne disinfecting system with at least one spray nozzle 20 mounted to the at least one connecting duct 14, wherein a supply hose 22/48 connects the at least one spray nozzle 20 to at least one reservoir 24/44/46 of disinfectant. The plurality of ultraviolet lights 114 include segments of ultraviolet lights configured as a plurality in a ring formation 108 within an inner perimeter of the at least one connecting duct 14 and mounted along a width and a height of the inner perimeter of the at least one connecting duct 14.

In a further exemplary embodiment, a system for disinfecting air circulated in an HVAC system, as shown in FIGS. 16A-28 and 33 is disclosed, including an interchangeable filter 92/102 located in a filter housing 62*a*/62*b*. The filter housing 62*a*/62*b* connects two segments of ductwork 14 as shown in FIGS. 18D-19C, 31A, and 33. The filter housing 62*a*/62*b* is contoured to align with perimeter dimensions of each of said two segments of ductwork 14. The filter housing 62*a*/62*b* defining a four-walled metallic segment as shown in FIGS. 20A-20D and 28A-28D, and contains openings correlating to each of said two segments of ductwork 14, as may be seen in the installed filter housing 62*b* from FIG. 31A. A closeable opening 74*a*/74*b* provides for insertion of the interchangeable filter 92/102 therein created by a hinge 68*a*/68*b* moveably coupling one wall of said four-walled metallic segment thereby creating a hinged flap as may be seen in FIGS. 20E and 31A, whereby once closed, the flap 66*a*/66*b* seals an inside airflow channel between each ductwork segment 14 connected by said four-walled metallic segment 62*a*/62*b*.

In some embodiments, the interchangeable filter is an ultraviolet light filter 102 as shown in FIGS. 25C and 30A-31C with ultraviolet lights 108 configured in a ring formation affixed to a removable frame 110 within an inner perimeter of the filter housing 62*b*, wherein the ultraviolet lights 108 are mounted along a width and a height of the frame 110, as may be seen.

In some embodiments, as shown in FIGS. 18C-25B, the interchangeable filter is an elongate three-dimensional grid 92 with a series of openings 98 to allow circulated air to flow over the air filter's elongate surfaces 96 and is pre-dipped in a disinfecting solution which is allowed to dry on the surfaces 96 of the interchangeable filter 92 to thereby kill any pathogen that may come in contact with said surfaces 96.

In some embodiments, as may be appreciated in FIGS. 8, 9, 13, and 33, the surfaces 96 of the interchangeable filter 92 are periodically sprayed with a disinfectant solution expelled through at least one spray nozzle 20 directed at the interchangeable filter 92 to thereby kill any pathogen that may come in contact with the surfaces 96 of the interchangeable filter 92, whereby the spray nozzle 20 is connected to a supply hose 22 that carries liquid disinfectant from a reservoir 24.

In some embodiments, the spray nozzle 20 is mounted to at least one segment of ductwork 14 of the two segments of ductwork. A spray ring 18 is further included, and defined by a perimeter hose 18 connecting the supply hose 22 to the at least one spray nozzle 20, wherein a plurality of spray nozzles 20 are mounted along the spray ring 18.

While there has been shown and described above the preferred embodiment of the instant invention it is to be appreciated that the invention may be embodied otherwise than is herein specifically shown and described and that certain changes may be made in the form and arrangement of the parts without departing from the underlying ideas or principles of this invention as set forth in the Claims appended herewith.

I claim:

1. A system for disinfecting air circulated in an HVAC system, comprising:

an interchangeable filter located in a filter housing, wherein said filter housing connects two segments of ductwork and said filter housing is contoured to align with perimeter dimensions of each of said two segments of ductwork;

said filter housing defining a four-walled metallic segment with openings correlating to each of said two segments of ductwork;

a closeable opening for insertion of said interchangeable filter therein created by a hinge moveably coupling one wall of said four-walled metallic segment thereby creating a hinged flap, said hinge being positioned along a top edge of said four-walled metallic segment and being affixed between said hinged flap and said four-walled metallic segment such that said hinged flap remains attached to said filter housing when opened and rotates about a fixed rotational axis extending along said top edge, whereby once closed, said flap seals an inside airflow channel between each ductwork segment connected by said four-walled metallic segment;

wherein said interchangeable filter is an ultraviolet light filter with ultraviolet lights configured in a ring formation affixed to a removable frame within an inner perimeter of said filter housing, wherein said ultraviolet lights are mounted along a width and a height of said frame and are positioned along a perimeter of said removable frame and directed inward toward an airflow passage defined through said filter housing such that ultraviolet light projects across said airflow passage on both an upstream side and a downstream side of said removable frame;

wherein said hinged flap includes a power aperture formed therethrough;

wherein an electrical inlet is mounted through said hinged flap; and wherein said removable frame includes an electrical connector positioned to electrically couple with said electrical inlet when said hinged flap is in a closed position.

* * * * *